US011672614B1

(12) United States Patent
Roh et al.

(10) Patent No.: US 11,672,614 B1
(45) Date of Patent: Jun. 13, 2023

(54) ROBOTIC SURGICAL SYSTEMS WITH MULTI-MODALITY IMAGING FOR PERFORMING SURGICAL STEPS

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael John Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/747,284

(22) Filed: May 18, 2022

(51) Int. Cl.
| | |
|---|---|
| *A61B 5/00* | (2006.01) |
| *A61B 34/20* | (2016.01) |
| *G16H 50/20* | (2018.01) |
| *G16H 30/20* | (2018.01) |
| *A61B 34/30* | (2016.01) |
| *A61B 34/00* | (2016.01) |

(52) U.S. Cl.
CPC ............ *A61B 34/20* (2016.02); *A61B 5/0035* (2013.01); *A61B 5/0036* (2018.08); *A61B 34/00* (2016.02); *A61B 34/30* (2016.02); *G16H 30/20* (2018.01); *G16H 50/20* (2018.01); *A61B 2034/2074* (2016.02)

(58) Field of Classification Search
CPC ..... A61B 34/20; A61B 5/0035; A61B 5/0036; A61B 34/00; A61B 34/30; A61B 2034/2074; G16H 30/20; G16H 50/20
See application file for complete search history.

(56) References Cited

U.S. PATENT DOCUMENTS

2020/0138360 A1\* 5/2020 Fan ...................... G06V 10/751
2021/0196425 A1\* 7/2021 Shelton, IV ......... A61B 1/0005

\* cited by examiner

*Primary Examiner* — Joel Lamprecht
(74) *Attorney, Agent, or Firm* — Perkins Coie LLP

(57) ABSTRACT

Methods, apparatuses, and systems for automated disease detection using multiple-wavelength imaging are disclosed. The disclosed system uses multiple imaging modalities for assessing a medical condition. Data collected from multiple cameras and imaging modalities is processed to identify common structures. The common structures are used to scale and align images, which are analyzed to detect one or more medical conditions. Each acquired image is assessed, and the resulting probabilities are consolidated. The images can be assessed together by using artificial intelligence and machine learning.

20 Claims, 16 Drawing Sheets

OPERATING ROOM DATABASE

| Patient | Heart Rate | SpO2 | Camera (.CSV) | Image Map (.CSV) | First Analyzer | Second Analyzer | Combined Probability Number |
|---|---|---|---|---|---|---|---|
| Alex | 82 | 98 | Image 1 | Image 11 | Image 21 | Image 31 | 0.7 |
| | 85 | 96 | Image 2 | Image 12 | Image 22 | Image 32 | 0.8 |
| | 88 | 90 | Image 3 | Image 13 | Image 23 | Image 33 | 0.8 |

*FIG. 8A*

SENSOR DATABASE

| S. No. | First Imaging Modality | Probability Number (Threshold range 0.6-1.0) | Second Image Modality | Probability Number | Combined Probability Number | Diagnosis for Osteoporosis |
|---|---|---|---|---|---|---|
| Patient 1 | Image 41 | 0.4 | Image 51 | 0.7 | 0.4 | Not feasible |
| Patient 2 | Image 42 | 0.6 | Image 52 | 0.8 | 0.8 | Low |
| Patient 3 | Image 43 | 0.7 | Image 53 | 0.8 | 0.7 | High |

*FIG. 8B*

|  | PET | Ultrasound | MRI | CT | Visible Light | Infrared (IR) | X-Ray |
|---|---|---|---|---|---|---|---|
| X-Ray | Heart Attack | Osteoporosis | Bone Degeneration | Bone Fractures | Bone Cyst | Skin Infections |  |
| Infrared | Bone Degeneration | Heart Disease | Hidradenitis suppurativa | Imaging of the brain | Infected Tissues |  |  |
| Visible Light | Bone Fractures | Bone Degeneration | Infectious Diseases | Trauma |  | Infected Tissues |  |
| CT | Cancer spread and treatment effectiveness | Musculoskeletal Disorders | Appendicitis |  | Trauma | Imaging of the brain |  |
| MRI | Imaging of the brain | Bone Cyst |  | Appendicitis | Infectious Diseases | Hidradenitis suppurativa |  |
| Ultrasound | Pregnancy monitoring and identification of complications |  | Bone Cyst | Musculoskeletal Disorders | Bone Degeneration | Heart Disease |  |
| PET |  |  |  |  |  |  |  |

*FIG. 10*

| X-Ray | Infrared | Visible Light | Computer Tomography | MRI | Ultrasound | PET |
|---|---|---|---|---|---|---|
| Disease | Breast Cancer | | Appendicitis | Cysts | Cysts | Prostate |
| Bone Degeneration | Diabetes | | Cancer | Tumour | Gallstone | Thyroid |
| Fractures | Neuropathy | | Trauma | Bleeding | Liver cancer | Lung cancer |
| Tumors | Peripheral vascular disorder | | Heart Disease | Swelling | Fatty Liver disease | Cervix |
| Infections | Dermatology | | Musculoskeletal Disorders | Brain abnormalities | Abnormal enlargement of Spleen | Colorectal tumours |
| | Fever Screening | | Infectious Diseases | Infections | Abnormal enlargement of Liver | Pancreatic tumours |

FIG. 11

| Wavelength (nm) | LIKELIHOOD OF INFECTION (%) Infrared Temperature (°F) | | | | | | | | | |
|---|---|---|---|---|---|---|---|---|---|---|
| | 98 | 98.5 | 99 | 99.5 | 100 | 100.5 | 101 | 101.5 | 102 |
| 750 | 1.6 | 9.4 | 18.6 | 35.7 | 49.8 | 64.2 | 76.4 | 89.3 | 84.0 |
| 725 | 1.3 | 8.4 | 17.7 | 31.3 | 44.6 | 60.3 | 72.0 | 85.2 | 88.5 |
| 700 | 1.1 | 6.4 | 13.8 | 29.6 | 36.8 | 52.1 | 68.9 | 83.7 | 95.3 |
| 675 | 0.8 | 4.9 | 11.6 | 23.4 | 53.3 | 62.0 | 72.6 | 82.5 | 86.4 |
| 650 | 0.6 | 4.3 | 7.6 | 21.7 | 36.4 | 57.2 | 52.4 | 68.2 | 72.9 |
| 625 | 0.5 | 3.4 | 4.8 | 19.4 | 29.4 | 52.6 | 47.5 | 43.2 | 45.2 |
| 600 | 0.3 | 2.1 | 3.6 | 15.6 | 21.6 | 43.8 | 32.8 | 24.3 | 31.2 |
| 575 | 0.2 | 1.2 | 2.4 | 12.5 | 19.6 | 32.4 | 28.9 | 26.0 | 22.8 |
| 550 | 0.1 | 0.8 | 1.1 | 8.6 | 12.3 | 24.5 | 13.2 | 15.5 | 12.7 |

| | LIKELIHOOD OF OSTEOPOROSIS (%) | | | | | |
|---|---|---|---|---|---|---|
| DEXA/X-Ray (g/cm2) | Photoacoustic/Ultrasound Intensity (a.u.) | | | | | |
| | | 1 | 2 | 3 | 4 | 5 |
| 0.5 | | 98.3 | 84.3 | 24.1 | 10.2 | 4.3 |
| 0.7 | | 86.1 | 72.4 | 16.2 | 8.1 | 2.4 |
| 0.9 | | 67.2 | 65.1 | 9.7 | 6.2 | 1.9 |
| 1.1 | | 32.1 | 24.6 | 6.4 | 3.2 | 1.5 |
| 1.3 | | 11.3 | 8.9 | 4.3 | 1.8 | 0.8 |
| 1.5 | | 4.1 | 5.3 | 3.2 | 0.9 | 0.2 |

LIKELIHOOD OF CANCEROUS TISSUE (%)

| | | PET (SUVmax) | | | | | | | |
|---|---|---|---|---|---|---|---|---|---|
| | | 1 | 2 | 3 | 4 | 5 | 6 | 7 | 8 |
| CT (Hounsfield units) | -600 | 0.1 | 0.1 | 0.1 | 0.2 | 0.4 | 0.9 | 1.2 | 0.6 |
| | -400 | 0.1 | 0.2 | 0.3 | 0.9 | 2.1 | 8.1 | 11.4 | 4.8 |
| | -200 | 0.2 | 2.5 | 12.1 | 24.8 | 18.7 | 23.6 | 42.1 | 22.7 |
| | 0 | 2.3 | 11.2 | 21.3 | 52.1 | 64.3 | 86.4 | 80.3 | 68.1 |
| | 200 | 1.8 | 7.3 | 18.4 | 44.1 | 58.1 | 84.3 | 76.1 | 62.1 |
| | 400 | 1.1 | 4.2 | 11.7 | 22.6 | 14.2 | 21.6 | 32.1 | 19.6 |
| | 600 | 0.4 | 1.2 | 3.5 | 3.8 | 7.1 | 9.4 | 11.6 | 8.3 |
| | 800 | 0.2 | 0.4 | 0.8 | 1.1 | 2.7 | 3.8 | 4.1 | 2.1 |
| | 1000 | 0.1 | 0.1 | 0.2 | 0.3 | 0.5 | 0.8 | 0.8 | 0.4 |

*FIG. 14*

ROBOTIC SURGICAL SYSTEMS WITH MULTI-MODALITY IMAGING FOR PERFORMING SURGICAL STEPS

TECHNICAL FIELD

The present disclosure is generally related to automated and robotic surgical procedures and specifically to apparatuses for performing robotic surgical procedures using automated disease detection by multiple-wavelength imaging.

BACKGROUND

More than 200 million surgeries are performed worldwide each year, and recent reports reveal that adverse event rates for surgical conditions remain unacceptably high, despite traditional patient safety initiatives. Adverse events resulting from surgical interventions can be related to errors occurring before or after the procedure, as well as technical surgical errors during the operation. For example, adverse events can occur due to (i) a breakdown in communication within and among the surgical team, care providers, patients, and their families; (ii) delays in diagnosis or failure to diagnose; and (iii) delays in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the health care team. However, conventional methods are typically insufficient to prevent surgical errors and adverse events during surgery.

BRIEF DESCRIPTION OF THE DRAWINGS

FIG. 8A illustrates a structure of an example database for automated disease detection using multiple-wavelength imaging, in accordance with one or more embodiments.

FIG. 8B illustrates a structure of an example database for automated disease detection using multiple-wavelength imaging, in accordance with one or more embodiments.

FIG. 10 illustrates a structure of an example data chart for analyzer combinations for automated disease detection using multiple-wavelength imaging, in accordance with one or more embodiments.

FIG. 11 illustrates a structure of an example data chart of a variety of disease states detectable by imaging modality for automated disease detection using multiple-wavelength imaging, in accordance with one or more embodiments.

FIG. 12 illustrates a structure of an example data chart, in accordance with one or more embodiments.

FIG. 14 illustrates a structure of an example data chart showing the likelihood of cancerous tissue in a localized area when using computer tomography (CT) and positron emission tomography (PET) for automated disease detection using multiple-wavelength imaging, in accordance with one or more embodiments.

DETAILED DESCRIPTION

Figure 1:
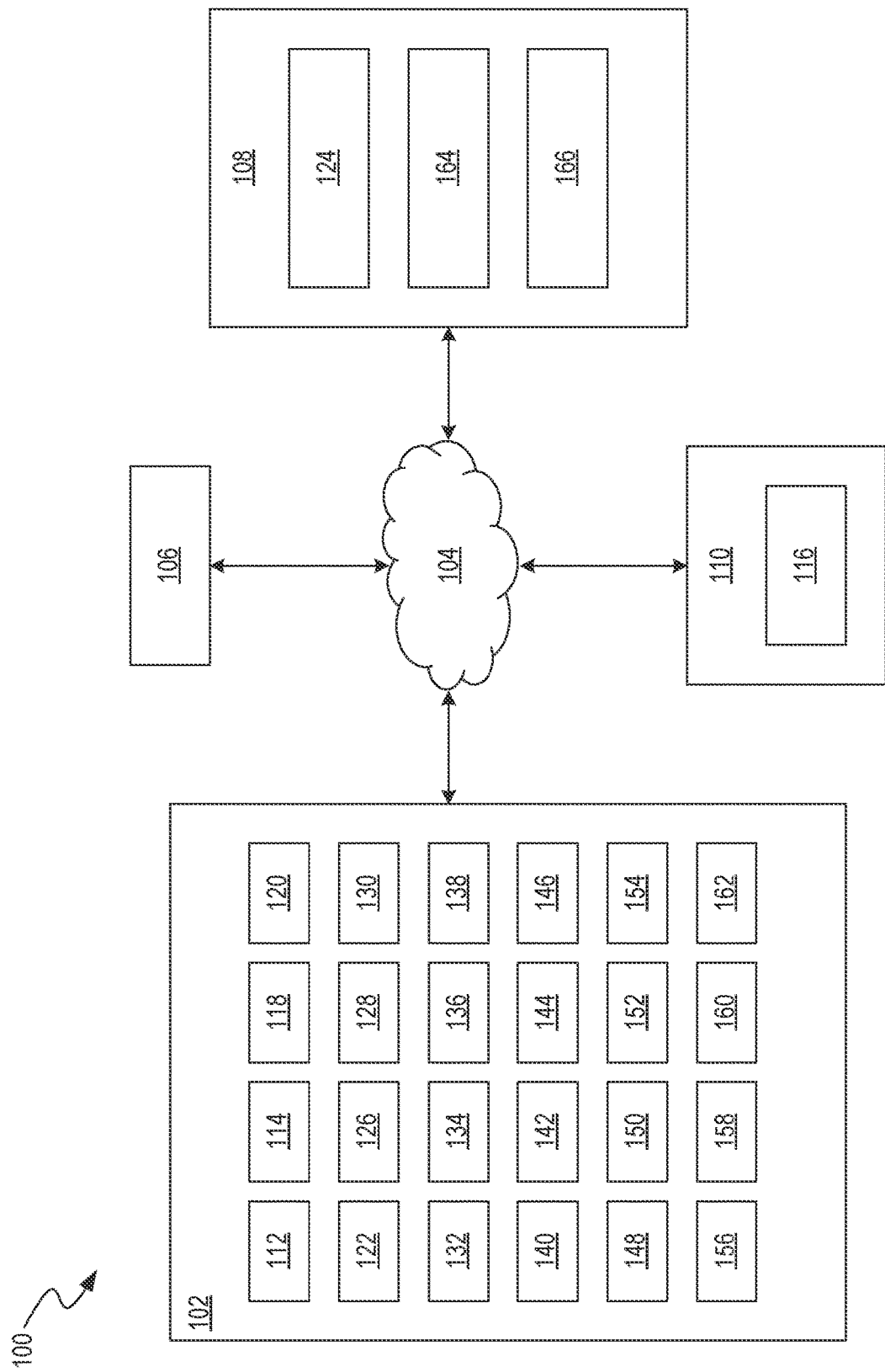
FIG. 1 is a block diagram illustrating an example surgical system, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples. Throughout this specification, plural instances (e.g., "610") can implement components, operations, or structures (e.g., "610*a*") described as a single instance. Further, plural instances (e.g., "610") refer collectively to a set of components, operations, or structures (e.g., "610*a*") described as a single instance. The description of a single component (e.g., "610*a*") applies equally to a like-numbered component (e.g., "610*b*") unless indicated otherwise. These and other aspects, features, and implementations can be expressed as methods, apparatuses, systems, components, program products, means or steps for performing a function, and in other ways. These and other aspects, features, and implementations will become apparent from the following descriptions, including the claims.

Using the embodiments disclosed herein, medical imaging is performed using different wavelengths of electromagnetic energy, ultrasounds, magnetic resonance, etc. The different wavelengths when directed towards a subject, such as bone tissue, soft tissue, or any other subject or substance, image different types of tissues with varying depths of penetration. For example, when visible light of a predefined wavelength is directed at bone tissue, a part of the incident light can be absorbed by the bone tissue. As a result, the intensity of the reflected/refracted light is less than that of the incident light. The decrease in the intensity of the incident light can be measured and used to generate an image. In embodiments, different medical devices having capabilities including, but not limited to, X-ray imaging, magnetic resonance imaging (MRI), ultrasound, angiography, or computer tomography (CT) are used. In embodiments, omni-tomographic imaging or grand fusion imaging, such as large-scale fusion of simultaneous data acquisition from multiple imaging modalities (e.g., CT, MRI, PET, SPECT, USG, or optical imaging), is used. Composite images, including image data from multiple modalities, are sometimes referred to as "multi-modality images" or "multiple-modality images" herein.

The embodiments disclosed herein describe methods, apparatuses, and systems for automated disease detection using multiple-wavelength imaging. In some embodiments, multiple imaging modalities are used for assessing a medical condition. Data collected from multiple cameras and imaging modalities are processed to identify common structures. The common structures are used to scale and align images, which are analyzed to detect one or more medical conditions. Each acquired image is assessed, and the resulting probabilities are consolidated. The images can be assessed together by using artificial intelligence and machine learning.

In some embodiments, a computer-implemented method for automated disease detection using multiple-wavelength imaging includes verifying the operability of medical equipment of a robotic surgical system. A fiduciary marker is placed in a region of interest of a patient's anatomy. First images of the region of interest are captured by a first imaging device of the medical equipment using a first imaging modality, wherein the fiduciary marker is visible in the first images. Second images of the region of interest are captured by a second imaging device of the medical equipment using a second imaging modality, wherein the fiduciary marker is visible in the second images. Tissue structures of the region of interest are identified using image processing performed on the first images and the second images by referencing the fiduciary marker. A first set of data points is determined describing the tissue structures using the first images. For example, the first set of data points can refer to two-dimensional (X,Y) data points, three-dimensional data points, or four-dimensional data points, etc. A second set of (X,Y) data points can be determined describing the tissue structures using the second images. The first set of (X,Y) data points and the second set of (X,Y) data points are fused. The medical condition of the patient and a confidence level are determined using a machine learning system by correlating the fused first set of (X,Y) data points and the second set of (X,Y) data points to stored patient data. Responsive to the confidence level exceeding a threshold, a surgical robot is updated with the fused first set of (X,Y) data points and the second set of (X,Y) data points for a surgical procedure to be performed on the region of interest by the surgical robot for treating the medical condition. Graphical visualizations of the fused first set of (X,Y) data points and the second set of (X,Y) data points are generated for use by a physician participating in the surgical procedure with the surgical robot.

The advantages and benefits of the methods, systems, and apparatuses disclosed herein include compatibility with best practice guidelines for performing surgery in an operating room, e.g., from regulatory bodies and professional standards organizations such as the Association for Surgical Technologists. The imaging systems disclosed use computer networks, the Internet, intranets, and supporting technologies to implement a cost-effective technology to collect, transmit, store, analyze, and use imaging information in electronic formats. As a result, surgical robots can use the embodiments to collect and analyze vast amounts of information, resulting in early diagnoses. The disclosed methods reduce the amount of noise and increase the resolution, replicability, efficiency, and accuracy in collecting and analyzing information. Further, the embodiments disclosed herein enable meta-analyses for more-elaborate diagnostic procedures and reduce the need for repetitive invasive diagnostic testing. In addition, the disclosed systems enable continuous monitoring and analysis of the health of the patient in order to provide real-time assistance to a surgical robot or surgeon during a surgical procedure.

Further, the omni-tomography imaging technologies disclosed offer synergy in vivo for diagnosis, intervention, and drug development. The embodiments can be implemented as an imaging platform for the development of systems biology and modern medicine. The disclosed imaging systems use different medical imaging modalities for more efficiently diagnosing medical conditions, such as a possible presence of a tumor. When a first method, such as X-rays, indicates the possible presence of a tumor, this is confirmed by another scanning method, such as a magnetic resonance imaging (MRI) method, computerized tomography (CT), or positron emission tomography (PET) scan. Thus error correction is achieved, and confidence levels for diagnosis and detection are increased.

Further, the methods disclosed provide a versatile and cost-effective determination of wavelengths for particular medical imaging applications. The disclosed systems provide efficient and improved quality results for disease stages in medical surgery. Further, the hyperspectral imaging techniques disclosed and the apparatus for analyzing subjects using hyperspectral image modules disclosed provide improved quality results for detecting disease states in medical surgery. The optional contact probe modules disclosed collect signals from suspected regions for medical diagnosis using the disclosed hyperspectral imaging technique system.

Further, the embodiments provide automated and more efficient systems for using multiple imaging modalities, especially those using different wavelengths of electromagnetic waves. Quicker diagnosis of patients is achieved compared to traditional methods via simultaneous or sequential imaging. The automated methods of aligning images taken using different imaging modalities disclosed provided improved analysis of the images to identify medical conditions. In addition, the advantages of the convolutional neural network (CNN) used for machine learning (ML) in the disclosed embodiments include the obviation of feature extraction and the use of shared weight in convolutional layers, which means that the same filter (weights bank) is used for each node in the layer; this both reduces memory footprint and improves performance.

Advantageously, the image analysis can be performed from a single imaging reference position or range of known positions (e.g., multiple locations having known relative positions to create a well-posed relationship) to enable position-independent correlating of values, images, and/or captured data. In embodiments, multiple-imaging devices are implemented. A multiple-imaging device can capture different images using different imaging modalities. In single imaging reference position embodiments, output from a multiple-imaging device can be directly combined to provide composite multi-modality analysis. For example, the system can select and process (e.g., using different weights, filters, etc.) output from one or more of the multiple-imaging devices. The processed output can then be combined with output (e.g., image data, images, video, etc.) from any other devices (e.g., imaging devices, CT scanners, cameras, X-ray machines, and the like). The relative positions between the imaging devices can be stored by the system. The system can then process the data (e.g., transform the data, modify or scale the data, etc.) to provide for enhanced interpretation by a physician. Transformation matrices can be stored to combine outputs from imaging devices located at different positions during tissue analysis. Advantageously, the transformation matrices allow for accurate analysis of the same tissues, features, or the like when using multiple-imaging devices. Further, the resulting composite analysis can then be overlaid onto image data to generate two-dimensional (2D) or three-dimensional (3D) multi-modality renderings, topological maps, pictures, video, or other image data to produce a diagnostic image or map, which can be annotated by a user or a system programmed for annotation, etc., to facilitate user review. The transformation matrices can be selected based on the modalities used to capture the images.

The resulting outputs can be selected and correlated to generate one or more diagnoses based on, for example, patient information (e.g., age, condition, status, etc.), accuracy scores for the individual values, machine-learning models, and/or various combinations thereof. The methods disclosed herein can correlate images (e.g., composite images, multi-modality images, single-modality images, etc.) to reference cases to identify similar individuals with known conditions. Then the reference cases (and the combined measurements) are used to diagnose an individual's condition. Accordingly, the systems and methods disclosed herein provide an accurate assessment of the individual's condition.

FIG. 1 is a block diagram illustrating an example surgical system 100, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The console 108 is the same as or similar to the console 420 illustrated and described in more detail with reference to FIG. 4A. The system 100 is implemented using the components of the example computer system 300 illustrated and described in more detail with reference to FIG. 3. Likewise, embodiments of the system 100 can include different and/or additional components or can be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or an outpatient surgery center.

In some embodiments, the system 100 includes one or more medical or surgical patient monitors 112. The monitors 112 can include a vital signs monitor (a medical diagnostic instrument), which can be a portable, battery-powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiological parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the body part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end-tidal $CO_2$ monitor or capnography monitor used for measurement of the level of carbon dioxide that is released at the end of an exhaled breath (referred to as end-tidal carbon dioxide, $ETCO_2$). An end-tidal $CO_2$ monitor or capnography monitor is widely used in anesthesia and intensive care. $ETCO_2$ can be calculated by plotting expiratory $CO_2$ with time. Further, $ETCO_2$ monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end-tidal $CO_2$ monitor can be configured as side stream (diverting) or mainstream (non-diverting). A diverting end-tidal $CO_2$ monitor transports a portion of a patient's respired gases from the sampling site to the end-tidal CO2 monitor, while a non-diverting end-tidal CO2 monitor does not transport gas away. Also, measurement by the end-tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in an artery, used in the operating room 102) for measurement. The non-invasive method (referred to as a sphygmomanometer) works by measurement of force exerted against arterial walls during (i) ventricular systole (i.e., systolic blood pressure occurs when the heart beats and pushes blood through the arteries) and (ii) ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as the bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate—the rate at which breathing occurs—and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can cause a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on the skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia, where the heart rate becomes faster, and bradycardia, where the heart rate becomes slower), coronary heart disease, heart attacks, or cardiomyopathy. The instrument used for measurement of the electrocardiogram is called an electrocardiograph, which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which helps in guiding a surgical robot during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP): the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 112 provide electromyography (EMG): the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation. Spontaneous EMG is recorded by the insertion of a needle electrode. Triggered EMG refers to the recording of myoelectric signals during stimulation of a target site such as a pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end effectors, cameras mounted to the ceiling or other surface above the surgical theater, or cameras mounted on a tripod or other independent mounting device. In some embodiments, the cameras are body worn by a surgical robot or other surgical staff, cameras are incorporated into a wearable device, such as an augmented reality device like Google Glass™, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably two-dimensional (2D) or three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Two-dimensional (2D) or three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by cutting a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. A surgical robot moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgical robot makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals across long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors include a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or LEDs. Surgical lights 122 include sterilizable handles, which allow a surgical robot to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery, which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engage with one another. When a telescope is used to operate on the abdomen, the procedure is called laparoscopy. The surgical tower 128 typically includes access to a variety of surgical tools, such as for electrocautery, radiofrequency, lasers, sensors, etc.

In some embodiments, radiofrequency (RF) is used in association with MIS devices. The RF can be used for the treatment of skin by delivering it to the skin through a minimally invasive surgical tool (e.g., fine needles), which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels that are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument can 130 consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools thereby minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of surgical tool-tissue interaction forces. During MIS, the field of view and workspace of surgical tools are compromised due to the indirect access to the anatomy and lack of surgeon's hand-eye coordination. The sensors 134 provide a tactile sensation to the surgeon by providing information regarding shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, magnetic resonance imaging (MRI), ultrasound, endoscopy, elastography, tactile imaging, thermography, medical photography, and nuclear medicine, e.g., positron emission tomography (PET). Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used are brain/spinal cord anomalies, tumors in the body, breast cancer screening, joint injuries, uterine/pelvic pain detection, or heart problems. For the creation of the image by an MRI instrument, magnetic resonance is produced by powerful magnets, which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI is more widely suitable for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses computed tomography imaging (CT) that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"—of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer, which produces sound waves and sends them into the body. The sound waves that are reflected are converted into electrical signals, which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgical robots in the placement of specialized surgical instruments and implants. The patient images are taken to guide a surgical robot before or during the medical procedure. The stereotactic navigation system 138 includes a camera having infrared sensors to determine the location of the tip of the probe being used in the surgical procedure. This information is sent in real-time so that the surgical robot has a clear image of the precise location where it is working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient and filters out expiratory carbon dioxide. The anesthesiology machine 140 can perform functions such as providing oxygen (02), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform; flex, or extend individual components of the platform; or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a post-operative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 100 includes a Jackson frame 144 (or Jackson table), which refers to a frame or table that is designed for use in spinal surgeries and can be used in a variety of spinal procedures in supine, prone, or lateral positions in a safe manner. Two peculiar features of the Jackson table 144 are the absence of central table support and an ability to rotate the table through 180 degrees. The Jackson table 144 is supported at both ends, which keeps the whole of the table free. This allows the visualization of a patient's trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (sometimes referred to as a Bair™ or Bair Hugger™). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets, which cover the patient. The blanket can be designed to use pressure points on the patient's body to prevent heat from reaching areas at risk for pressure sores or burns. The blanket can also include drainage holes where fluid passes through the surface of the blanket to linen underneath, which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The sequential compression device 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors that can contribute to poor quality in the environment of the operating room 102 are temperature, ventilation, and humidity, and those conditions can lead to profound effects on the health and work productivity of people in the operating room 102. As an example: surgeons prefer a cool, dry climate since they work under bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter (HEPA filter). A HEPA filter protects a patient from infection and contamination using a filter, which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The surgical tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system that controls the muscles). A major percentage of orthopedic tools are made of plastic. The orthopedic tools can be divided into the following specialties: hand and wrist, foot and ankle, shoulder, and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a surgical tool designed to gradually correct a deformity, e.g., corsets, splints, orthopedic footwear, insoles, and other devices to correct abnormal positions of the foot. A compression-distraction tool refers to a surgical tool designed to correct acquired or congenital deformities of the extremities, e.g., curvature, shortening, and pseudarthrosis such as Gudushauri. A fixation tool can be an internal fixation tool (e.g., screws, plates) or external fixation tools used to correct a radius or tibia fracture. The orthopedic tools can be boneholding forceps, drill bits, nail pins, hammers, staples, etc.

In some embodiments, the surgical tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can include a physical drill, power cord, electronically motorized bone drill, or rotating bone shearing incision work unit.

In some embodiments, the surgical tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be either absorbable (the stitches automatically break down harmlessly in the body over time without intervention) or non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the surgical tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, surgical tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as a sensor/transducer, a signal conditioner, a display, or a data storage unit, etc. In some embodiments, the medical equipment includes a sensor to receive a signal from instruments measuring a patient's body, a transducer for converting one form of energy to electrical energy, a signal conditioner such as an amplifier, filter, etc., to convert the output from the transducer into an electrical value, a display to provide a visual representation of the measured parameter or quantity, or a storage system to store data, which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. A ventilator is required when a person is not able to breathe on their own. A ventilator can perform a function of gently pushing air into the lungs and allow it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc. The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor, which generates a continuous stream of pressurized air that travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. A CPAP instrument can include a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment. The consumables 158 can include gloves, gowns, masks, syringes, needles, sutures, staples, tubing, catheters, or adhesives for wound dressing, in addition to other surgical tools needed by surgical robots, doctors, and nurses to provide care. Depending on the device, mechanical testing can be carried out in tensile, compression, or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries can be performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light-illuminated and the image seen with the microscope 116 is two-dimensional), dissection or stereoscope (light-illuminated and the image seen with the microscope 116 is three-dimensional), confocal (laser-illuminated and the image seen with the microscope 116 is on a digital computer screen), scanning electron (SEM) (electron-illuminated and the image seen with the microscope 116 is in black and white), or transmission electron microscope (TEM) (electron-illuminated and the image seen with the microscope 116 is the high magnification and high resolution).

The system 100 includes an electronic health records (EHR) database 106 that contains patient records. The EHR is a digital version of patients' paper charts. The EHR database 106 can contain more information than a traditional patient chart, including, but not limited to, a patient's medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected, and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker (e.g., the speaker 632 of FIG. 6), etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

Figure 2:
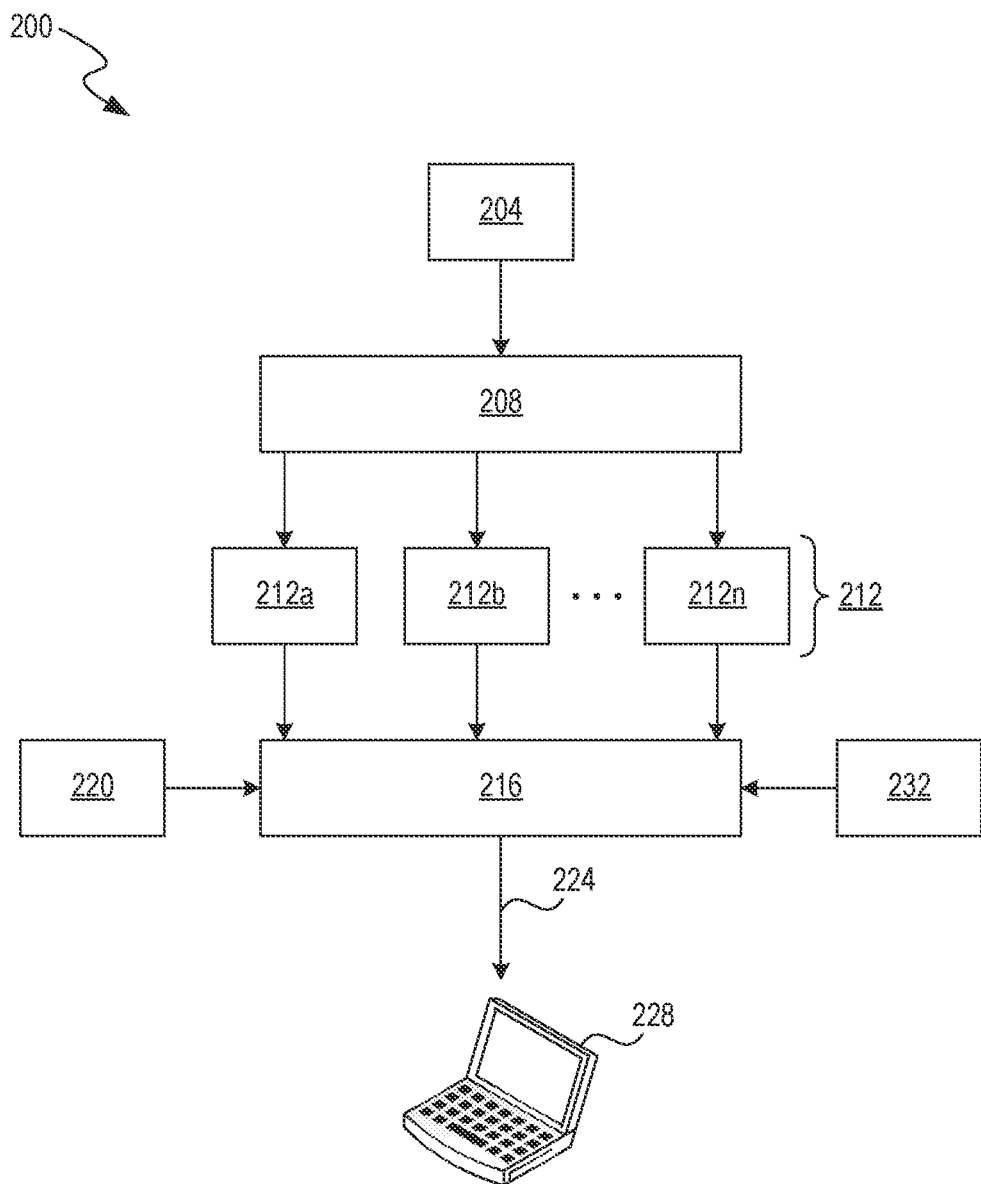
FIG. 2 is a block diagram illustrating an example machine learning (ML) system, in accordance with one or more embodiments.

FIG. 2 is a block diagram illustrating an example machine learning (ML) system 200, in accordance with one or more embodiments. The ML system 200 is implemented using components of the example computer system 300 illustrated and described in more detail with reference to FIG. 3. For example, the ML system 200 can be implemented on the console 108 using instructions programmed in the memory 164 illustrated and described in more detail with reference to FIG. 1. Likewise, embodiments of the ML system 200 can include different and/or additional components or be connected in different ways. The ML system 200 is sometimes referred to as a ML module.

The ML system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, . . . , 212n. The feature extraction module 208 reduces the redundancy in the input data 204, e.g., repetitive data values, to transform the input data 204 into the reduced set of features 212, e.g., features 212a, 212b, . . . , 212n. The feature vector 212 contains the relevant information from the input data 204, such that events or data value thresholds of interest can be identified by the ML model 216 by using this reduced representation. In some example embodiments, the following dimensionality reduction techniques are used by the feature extraction module 208: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the ML system 200. For example, the ML model 216 can use a cascade of multiple layers of nonlinear processing units for implicit feature extraction and transformation. Each successive layer uses the output from the previous layer as input. The ML model 216 can thus learn in supervised (e.g., classification) and/or unsupervised (e.g., pattern analysis) modes. The ML model 216 can learn multiple levels of representations that correspond to different levels of abstraction, wherein the different levels form a hierarchy of concepts. In this manner, the ML model 216 can be configured to differentiate features of interest from background features.

In alternative example embodiments, the ML model 216, e.g., in the form of a CNN generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker (e.g., the speaker 632 of FIG. 6), etc., implemented using components of the example computer system 300 illustrated and described in more detail with reference to FIG. 3. In some embodiments, the steps performed by the ML system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted area of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 216 can be a CNN that includes both convolutional layers and max pooling layers. The architecture of the ML model 216 can be "fully convolutional," which means that variable sized sensor data vectors can be fed into it. For all convolutional layers, the ML model 216 can specify a kernel size, a stride of the convolution, and an amount of zero padding applied to the input of that layer. For the pooling layers, the model 216 can specify the kernel size and stride of the pooling.

In some embodiments, the ML system 200 trains the ML model 216, based on the training data 220, to correlate the feature vector 212 to expected outputs in the training data 220. As part of the training of the ML model 216, the ML system 200 forms a training set of features and training labels by identifying a positive training set of features that have been determined to have a desired property in question, and, in some embodiments, forms a negative training set of features that lack the property in question.

The ML system 200 applies ML techniques to train the ML model 216, that when applied to the feature vector 212, outputs indications of whether the feature vector 212 has an associated desired property or properties, such as a probability that the feature vector 212 has a particular Boolean property, or an estimated value of a scalar property. The ML system 200 can further apply dimensionality reduction (e.g., via linear discriminant analysis (LDA), PCA, or the like) to reduce the amount of data in the feature vector 212 to a smaller, more representative set of data.

The ML system 200 can use supervised ML to train the ML model 216, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The ML system 200 applies the trained ML model 216 to the features of the validation set 232 to quantify the accuracy of the ML model 216. Common metrics applied in accuracy measurement include: Precision and Recall, where Precision refers to a number of results the ML model 216 correctly predicted out of the total it predicted, and Recall is a number of results the ML model 216 correctly predicted out of the total number of features that had the desired property in question. In some embodiments, the ML system 200 iteratively re-trains the ML model 216 until the occurrence of a stopping condition, such as the accuracy measurement indication that the ML model 216 is sufficiently accurate, or a number of training rounds having taken place. The validation set 232 can include data corresponding to confirmed anatomical features, tissue states, tissue conditions, diagnoses, or combinations thereof. This allows the detected values to be validated using the validation set 232. The validation set 232 can be generated based on analysis to be performed.

Figure 3:
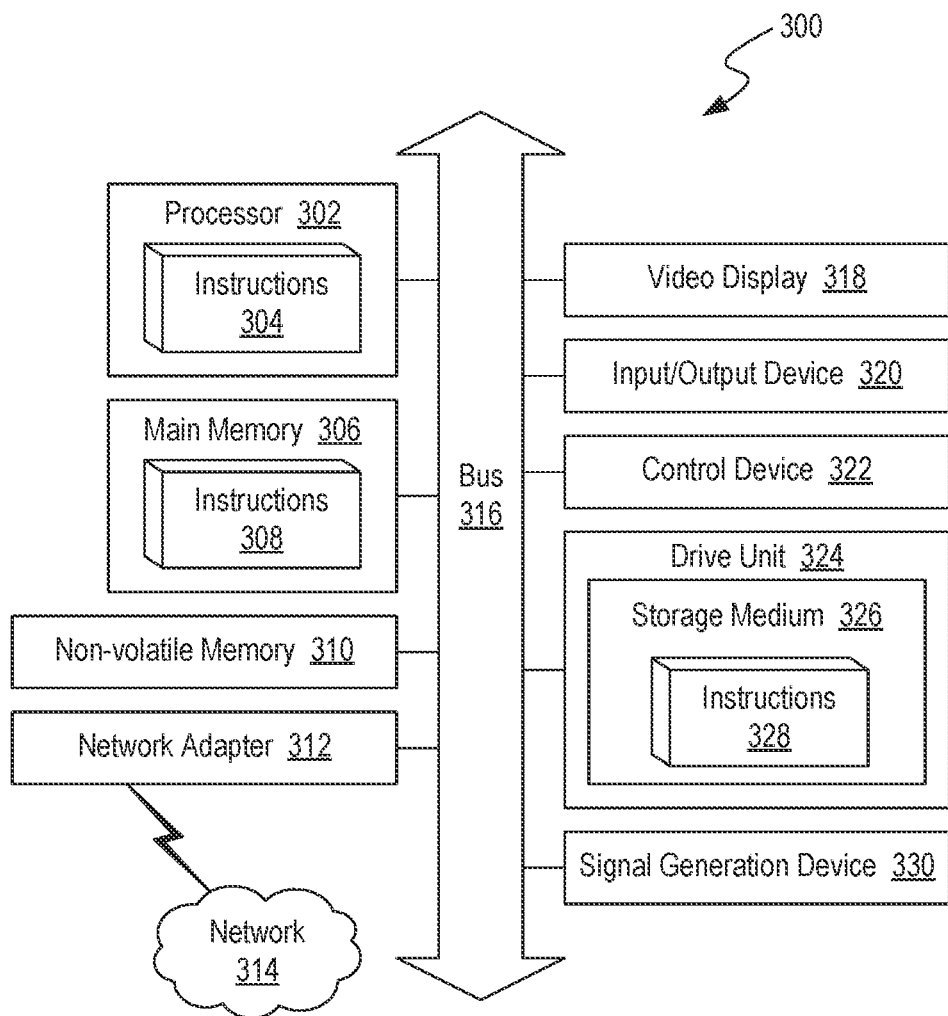
FIG. 3 is a block diagram illustrating an example computer system, in accordance with one or more embodiments.

FIG. 3 is a block diagram illustrating an example computer system, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the ML system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multilayer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4A:
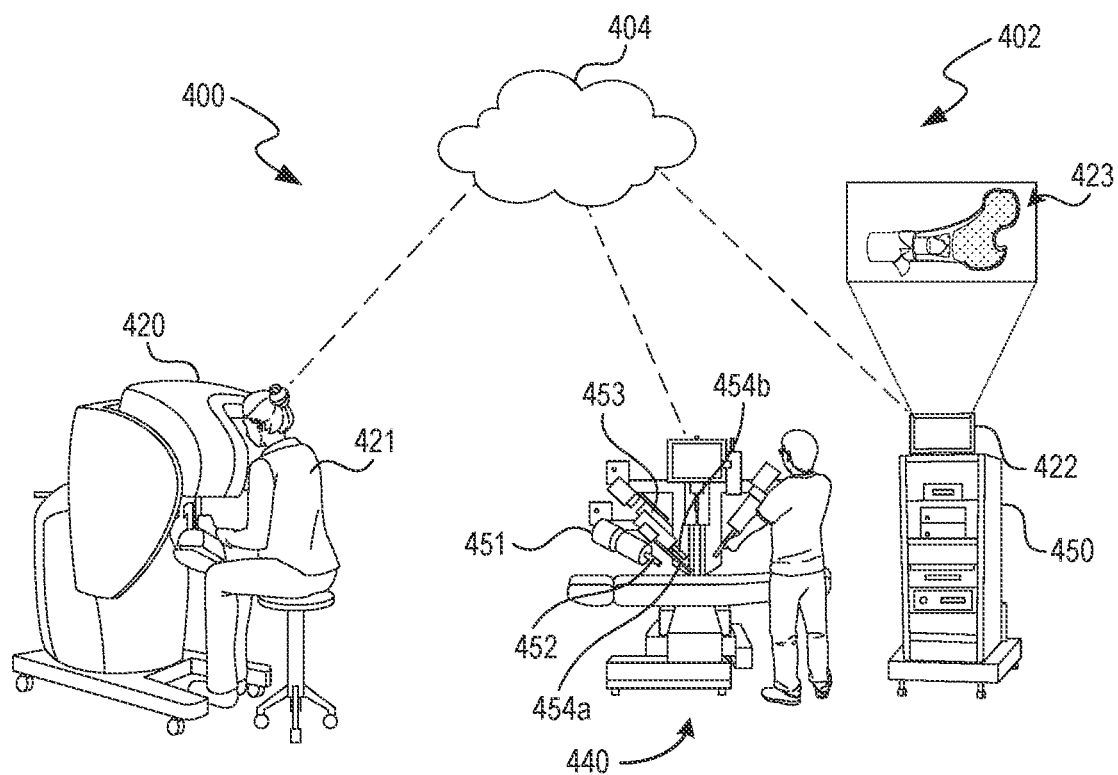
FIG. 4A is a block diagram illustrating an example robotic surgical system, in accordance with one or more embodiments.

FIG. 4A is a block diagram illustrating an example robotic surgical system 400, in accordance with one or more embodiments. The robotic surgical system 400 is the same as or similar to the robotic surgical system 160 illustrated and described in more detail with reference to FIG. 1. The robotic surgical system 400 can include components and features discussed in connection with FIGS. 1-3 and 4B-5. For example, the robotic surgical system 400 can include a console 420 with features of the console 108 of FIG. 1. Likewise, the components and features of FIG. 4A can be included or used with other embodiments disclosed herein. For example, the description of the input devices of FIG. 4A applies equally to other input devices (e.g., input devices 166 of FIG. 1).

The robotic surgical system 400 includes a user device or console 420 ("console 420"), a surgical robot 440, and a computer or data system 450. The console 420 can be operated by a surgeon and can communicate with components in an operating room 402, remote devices/servers, a network 404, or databases (e.g., database 106 of FIG. 1) via the network 404. The robotic surgical system 400 can include surgical control software and can include a guidance system (e.g., ML guidance system, AI guidance system, etc.), surgical planning software, event detection software, surgical tool software, etc. or other features disclosed herein to perform surgical step(s) or procedures or implement steps of processes discussed herein.

The user 421 can use the console 420 to view and control the surgical robot 440. The console 420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 420 can include a clutch pedal to allow the user 421 to disengage one or more sensor-actuator components from control by the surgical robot 440. The console 420 can also include display or output so that the one of more users can observe the patient being operated on, or the product being assembled, for example. In some embodiments, the display can show images, such as, but not limited to, medical images, video, etc. For surgical applications, the images could include, but are not limited to, real-time optical images, real-time ultrasound, real-time OCT images and/or other modalities, or could include pre-operative images, such as MRI, CT, PET, etc. The various imaging modalities can be selectable, programmed, superimposed, and/or can include other information superimposed in graphical and/or numerical or symbolic form.

The robotic surgical system 400 can include multiple consoles 420 to allow multiple users to simultaneously or sequentially perform portions of a surgical procedure. The term "simultaneous" herein refers to actions performed at the same time or in the same surgical step. The number and configuration of consoles 420 can be selected based on the surgical procedure to be performed, number and configurations of surgical robots, surgical team capabilities, or the like.

Figure 4B:
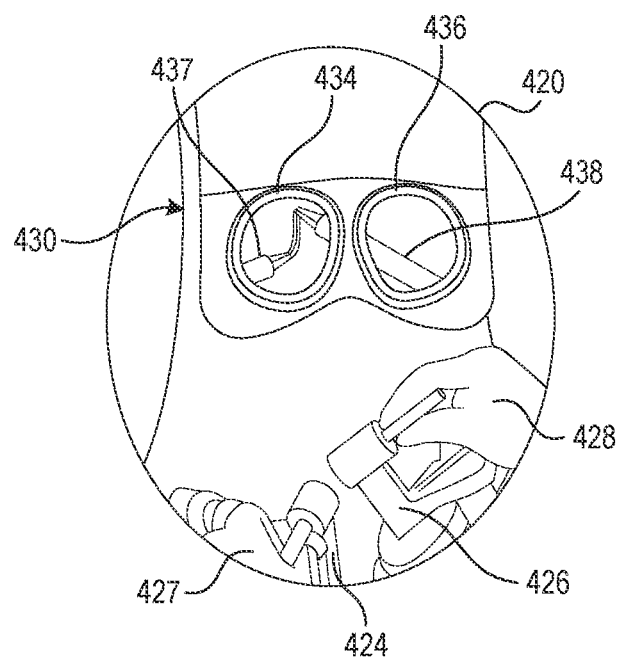
FIG. 4B illustrates an example console of the robotic surgical system of FIG. 4A, in accordance with one or more embodiments.

FIG. 4B illustrates an example console 420 of the robotic surgical system 400 of FIG. 4A, in accordance with one or more embodiments. The console 420 includes hand-operated input devices 424, 426, illustrated held by the user's left and right hands 427, 428, respectively. A viewer 430 includes left and right eye displays 434, 436. The user can view, for example, the surgical site, instruments 437, 438, or the like. The user's movements of the input devices 424, 426 can be translated in real-time to, for example, mimic the movement of the user on the viewer 430 and display (e.g., display 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 420 can be located at the surgical room or at a remote location.

The viewer 430 can display at least a portion of a surgical plan, including multiwavelength images, image modality information, fused data sets, tissue types, mapped images (e.g., tissue types maps, bone tissue maps, tissue density maps, diseased tissue maps, tissue condition maps, etc.), past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 430 can be a VR/AR headset, display, or the like. The robotic surgical system 400, illustrated and described in more detail with reference to FIG. 4A, can further include multiple viewers 430 so that multiple members of a surgical team can view the surgical procedure. The number and configuration of the viewers 430 can be selected based on the configuration and number of surgical robots.

Referring again to FIG. 4A, the surgical robot 440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 440 can be selected based on the procedures to be performed.

The surgical robot 440 can operate in different modes selected by a user, set by the surgical plan, and/or selected by the robotic surgical system 400. In some procedures, the surgical robot 440 can remain in the same mode throughout a surgical procedure. In other procedures, the surgical robot 440 can be switched between modes any number of times. The configuration, functionality, number of modes, and type of modes can be selected based on the desired functionality and user control of the robotic surgical system 400. The robotic surgical system 400 can switch between modes based on one or more features, such as triggers, notifications, warnings, events, etc. Different example modes are discussed below. A trigger can be implemented in software to execute a jump to a particular instruction or step of a program. A trigger can be implemented in hardware, e.g., by applying a pulse to a trigger circuit.

In a user control mode, a user 421 controls, via the console 420, movement of the surgical robot 440. The user's movements of the input devices can be translated in real-time into movement of end effectors 452 (one identified).

In a semi-autonomous mode, the user 421 controls selected steps and the surgical robot 440 autonomously performs other steps. For example, the user 421 can control one robotic arm to perform one surgical step while the surgical robot 440 autonomously controls one or more of the other arms to concurrently perform another surgical step. In another example, the user 421 can perform steps suitable for physician control. After completion, the surgical robot 440 can perform steps involving coordination between three or more robotic arms, thereby enabling complicated procedures. For example, the surgical robot 440 can perform steps involving four or five surgical arms, each with one or more end effectors 452. The surgical robot 440 can include a multi-modality imager 453 having imaging devices 454a, 454b (collectively "imaging devices 454"). The imaging devices 454 can be, for example, PET scanners, ultrasound imagers, MRI imagers, CT scanners, cameras (e.g., camera imager hardware, digital cameras, etc.), infrared imagers, etc. In embodiments, the surgical robot 440 retrieves/receives images from standalone X-ray machines, MRI machines, CT scanners, etc. Example imaging devices are discussed in connection with FIGS. 6A, 8A-8B, and 10-14. The number, imaging capabilities, and configurations of the imaging devices 454 can be selected based on the imaging to be performed.

The robotic surgical system 400 can automatically generate multi-modality images based on surgical plans and then perform one or more surgical steps of a planned surgical procedure. In embodiments, the robotic surgical system 400 analyzes a surgical plan for a patient to generate an imaging plan for obtaining patient information for diagnostic purposes, modifying the surgical plan, performing surgical steps (e.g., one surgical step, multiple surgical steps, all surgical steps), etc. The imaging plan can include, without limitation, one or more regions of interest, targeted information, predicted features of interest, information for diagnostic purposes, or the like. The robotic surgical system 400 can generate the imaging plan based on imaging capabilities of the multi-modality imager 453. The robotic surgical system 400 can notify the surgical team to add or replace imaging devices 454 to achieve the desired imaging capability.

The robotic surgical system 400 can retrieve available images of a patient from, for example, electronic medical records, image databases, and/or other imaging sources. The robotic surgical system 400 can identify and retrieve images that can be processed for producing one or more multi-modality images. The robotic surgical system 400 can determine whether additional unavailable images could be useful for generating multi-modality images that (1) meet at least one threshold criteria (e.g., a confidence score), (2) identify features of interest, (3) have diagnostic capability criteria, etc. In some procedures, the robotic surgical system 400 retrieves available images and determines imaging programs or parameters (e.g., positions, imaging settings, etc.) of one or more of the imaging devices 454 corresponding to the available images. In embodiments, a machine learning system (see FIG. 2) can be used to generate imaging plans based on training sets. The training sets can include, for example, single modality training sets, composite multi-modality training sets, confirmed diagnostic training sets, and other training sets. This allows the robotic surgical system 400 to perform re-training procedures for continuously or periodically training the machine learning system. Newly-captured images can be keyed to or matched with the retrieved images, thereby increasing accuracy of the multi-modality images. During intro-operative imaging, the images can be analyzed in real-time to further control the robotic surgical system 400.

In an autonomous mode, the surgical robot 440 can autonomously perform steps under the control of the data system 450. The robotic surgical system 400 can be pre-programmed with instructions for performing the steps autonomously. For example, command instructions can be generated based on a surgical plan. The surgical robot 440 autonomously performs steps or the entire procedure. The user 421 and surgical team can observe the surgical procedure to modify or stop the procedure. Advantageously, complicated procedures can be autonomously performed without user intervention to enable the surgical team to focus and attend to other tasks. Although the robotic surgical system 400 can autonomously perform steps, the surgical team can provide information in real-time that is used to continue the surgical procedure. The information can include surgical robot input, surgical team observations, and other data input.

The robotic surgical system 400 can also adapt to the user control to facilitate completion of the surgical procedure. In some embodiments, the robotic surgical system 400 can monitor, via one or more sensors, at least a portion of the surgical procedure performed by the surgical robot 440. The robotic surgical system 400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 400 can perform one or more actions based on the identified event. The actions can include, without limitation, modification of the surgical plan to address the potential adverse surgical event, thereby reducing the risk of the event occurring. The adverse surgical event can include one or more operating parameters approaching respective critical thresholds, as discussed in connection with FIG. 12. The adverse surgical events can be identified using a machine learning model trained using, for example, prior patient data, training sets (e.g., tool data), etc.

In some embodiments, the robotic surgical system 400 determines whether a detected event (e.g., operational parameters outside a target range or exceeding a threshold, etc.) is potentially an adverse surgical event based on one or more criteria set by the robotic surgical system 400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 400 can take other actions in response to identification of an event. If the robotic surgical system 400 identifies an end effector malfunction or error, the robotic surgical system 400 can stop usage of the end effector and replace the malfunctioning component (e.g., surgical tool or equipment) to complete the procedure. The robotic surgical system 400 can monitor hospital inventory, available resources in the surgical room 402, time to acquire equipment (e.g., time to acquire replacement end effectors, surgical tools, or other equipment), and other information to determine how to proceed with surgery. The robotic surgical system 400 can generate multiple proposed surgical plans for continuing with the surgical procedure. The user and surgical team can review the proposed surgical plans to select an appropriate surgical plan. The robotic surgical system 400 can modify a surgical plan with one or more corrective surgical steps based on identified surgical complications, sensor readings, or the like. The surgical steps include, without limitation, cauterizing, cutting tissue, clamping tissue, stapling tissue, excising tissue, implanting items, alternative steps to replace planned surgical steps, manipulating tissue, or other steps disclosed herein. The surgical steps can be selected to keep the patient's vital(s) within a target range, for example, based on one or more surgical criteria (e.g., overall surgical time, length of surgical step, etc.).

The robotic surgical system 400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-site and off-site simulations (e.g., pre-, or post-operative virtual simulations, simulations using models, etc.) can be generated and collected.

The surgical robot 440 can include robotic arms 451 (one identified) with robotic links, motors, and integrated or removable end effectors 452 (one identified). The end effectors 452 can include, without limitation, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or surgical tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 440 to provide more intelligent and intuitive results.

The data system 450 can improve surgical planning, monitoring (e.g., via the display 422), data collection, surgical robotics/navigation systems, intelligence for selecting instruments, implants, etc. The data system 450 can execute, for example, surgical control instructions or programs for a guidance system (e.g., ML guidance system, AI guidance system, etc.), surgical planning programs, event detection programs, surgical tool programs, etc. For example, the data system 450 can increase procedure efficiency and reduce surgery duration by providing information insertion paths, surgical steps, or the like. The data system 450 can be incorporated into or include other components and systems disclosed herein. As shown by FIG. 4A, the display 422 can display, for example, a diagnosis of tissue, images, maps, surgical plans, etc. For example, the display 422 can display a diagnostic image or map showing, for example, a bone in image 423 (discussed in more detail below with reference to multi-modality imaging), regions of interest (e.g., zones of diseased tissue, regions of tissue with specific characteristic(s), margins, etc.), features of interest, anatomical elements (e.g., cartilage, soft tissue, etc.), or the like. An example image is discussed in connection with FIG. 15. In some embodiments, a diagnostic image can include tissue density, tissue state, identified disease tissue, or the like. The system 402 can use the displayed data to perform one or more surgical steps. A user can view the display 422 to confirm the position of the tissue during the procedure.

The robotic surgical system 400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems can be used with many different systems for conducting robotic or minimally invasive surgery. One example of a surgical system and surgical robots which can incorporate methods and technology is the DAVINCI™ system available from Intuitive Surgical, Inc.™ of Mountain View, Calif. However, other surgical systems, robots, and apparatuses can be used.

The robotic surgical system 400 can perform one or more simulations using selected entry port placements and/or robot positions, to allow a surgeon or other user to practice procedures. The practice session can be used to generate, modify, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operatively or intraoperatively.

Embodiments can provide a means for mapping the surgical path for neurosurgery procedures that minimize damage through artificial intelligence mapping. The software for artificial intelligence is trained to track the least destructive pathway. A surgical robot can make an initial incision based on a laser marking on the skin that illuminates the optimal site. Next, a robot can make a small hole and insert surgical equipment (e.g., guide wires, cannulas, etc.) that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and posttreatment mapping can be compared by the surgeon and/or ML/AI system. The comparison can be used to determine next steps in a procedure and/or further train the ML/AI system.

Figure 5:
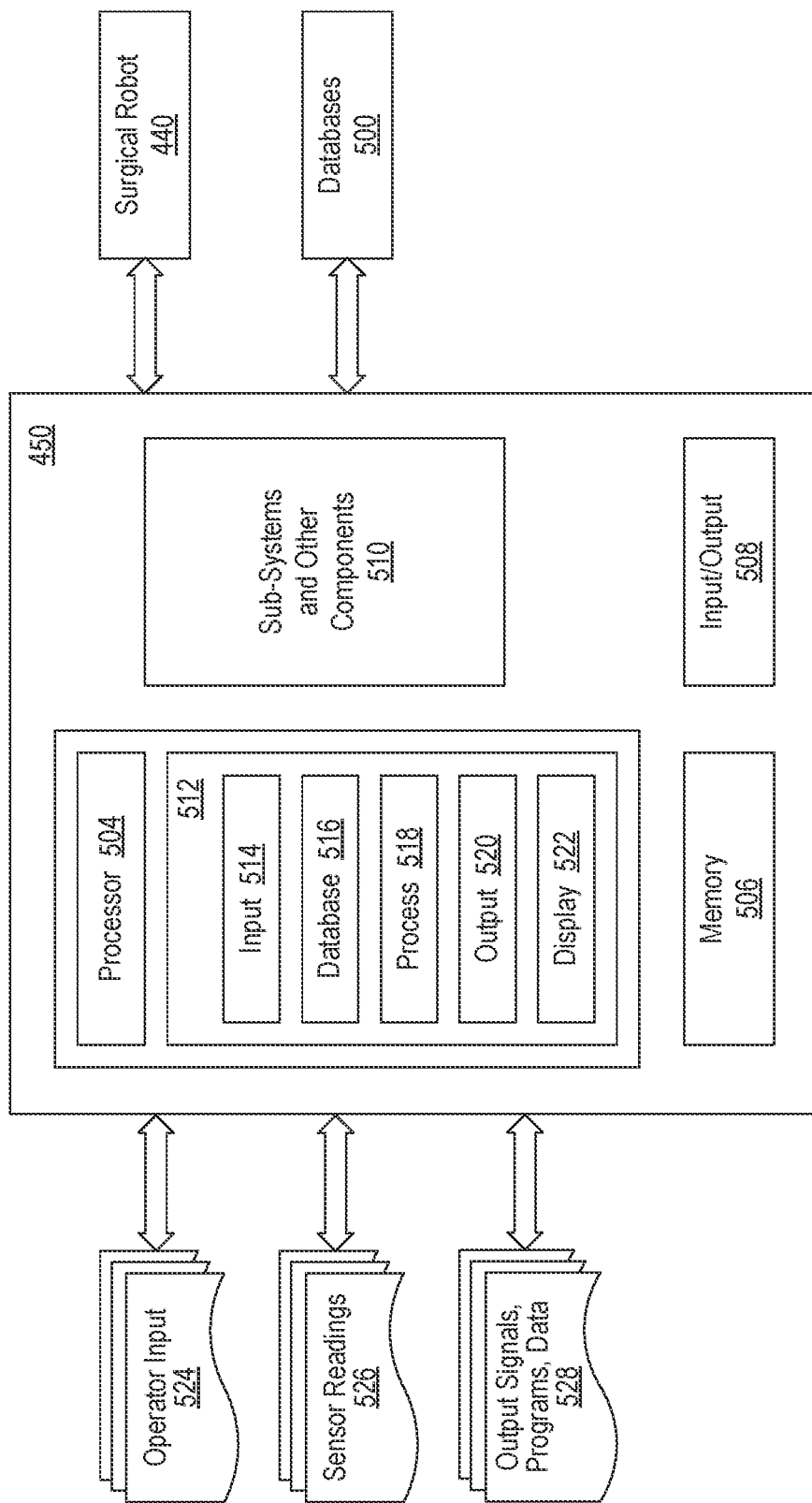
FIG. 5 is a schematic block diagram illustrating subcomponents of the robotic surgical system of FIG. 4A, in accordance with one or more embodiments.

FIG. 5 is a schematic block diagram illustrating subcomponents of the robotic surgical system 400 of FIG. 4A in accordance with embodiment of the present technology. The data system 450 has one or more processors 504, a memory 506, input/output devices 508, and/or subsystems and other components 510. The processor 504 can perform any of a wide variety of computing processing, image processing, robotic system control, plan generation or modification, and/or other functions. Components of the data system 450 can be housed in a single unit (e.g., within a hospital or surgical room) or distributed over multiple, interconnected units (e.g., though a communications network). The components of the data system 450 can accordingly include local and/or devices.

As illustrated in FIG. 5, the processor 504 can include a plurality of functional modules 512, such as software modules, for execution by the processor 504. The various implementations of source code (i.e., in a conventional programming language) can be stored on a computer-readable storage medium or can be embodied on a transmission medium in a carrier wave. The modules 512 of the processor 504 can include an input module 514, a database module 516, a process module 518, an output module 520, and, optionally, a display module 524 for controlling the display.

In operation, the input module 514 accepts an operator input 524 via the one or more input devices, and communicates the accepted information or selections to other components for further processing. The database module 516 organizes plans (e.g., robotic control plans, surgical plans, etc.), records (e.g., maintenance records, patient records, historical treatment data, etc.), surgical equipment data (e.g., instrument specifications), control programs, and operating records and other operator activities, and facilitates storing and retrieving of these records to and from a data storage device (e.g., internal memory 506, external databases, etc.). Any type of database organization can be utilized, including a flat file system, hierarchical database, relational database, distributed database, etc.

In the illustrated example, the process module 518 can generate control variables based on sensor readings 526 from sensors (e.g., end effector sensors of the surgical robot 440, patient monitoring equipment, etc.), operator input 524 (e.g., input from the surgeon console 420 and/or other data sources), and the output module 520 can communicate operator input to external computing devices and control variables to controllers. The display module 522 can be configured to convert and transmit processing parameters, sensor readings 526, output signals 528, input data, treatment profiles and prescribed operational parameters through one or more connected display devices, such as a display screen, touchscreen, printer, speaker system, etc.

In various embodiments, the processor 504 can be a standard central processing unit or a secure processor. Secure processors can be special-purpose processors (e.g., reduced instruction set processor) that can withstand sophisticated attacks that attempt to extract data or programming logic. The secure processors cannot have debugging pins that enable an external debugger to monitor the secure processor's execution or registers. In other embodiments, the system can employ a secure field-programmable gate array, a smartcard, or other secure devices.

The memory 506 can be standard memory, secure memory, or a combination of both memory types. By employing a secure processor and/or secure memory, the system can ensure that data and instructions are both highly secure and sensitive operations such as decryption are shielded from observation. In various embodiments, the memory 506 can be flash memory, secure serial EEPROM, secure field-programmable gate array, or secure application-specific integrated circuit. The memory 506 can store instructions for causing the surgical robot 440 to perform acts disclosed herein.

The input/output device 508 can include, without limitation, a touchscreen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. For example, if an applicator moves an undesirable amount during a treatment session, the input/output device 508 can alert the subject and/or operator via an audible alarm. The input/output device 508 can be a touch screen that functions as both an input device and an output device.

The data system 450 can output instructions to command the surgical robot 440 and communicate with one or more databases 2600. The surgical robot 440 or other components disclosed herein can communicate to send collected data (e.g., sensor readings, instrument data, surgical robot data, etc.) to the database 500. This information can be used to, for example, create new training data sets, generate plans, perform future simulations, post-operatively analyze surgical procedures, or the like. The data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between surgical equipment within the surgical room.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 440. For example, mode switching programs can include threshold or configuration settings for determining when to switch the mode of operation of the surgical robot 440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to optimize patient outcome, reduce or limit the risk of surgical complications, mitigate adverse events, manage costs for surgical procedures, reduce recovery time, or the like. The healthcare provider can modify how plans are generated over time to further optimize based on one or more criteria.

Figure 6A:
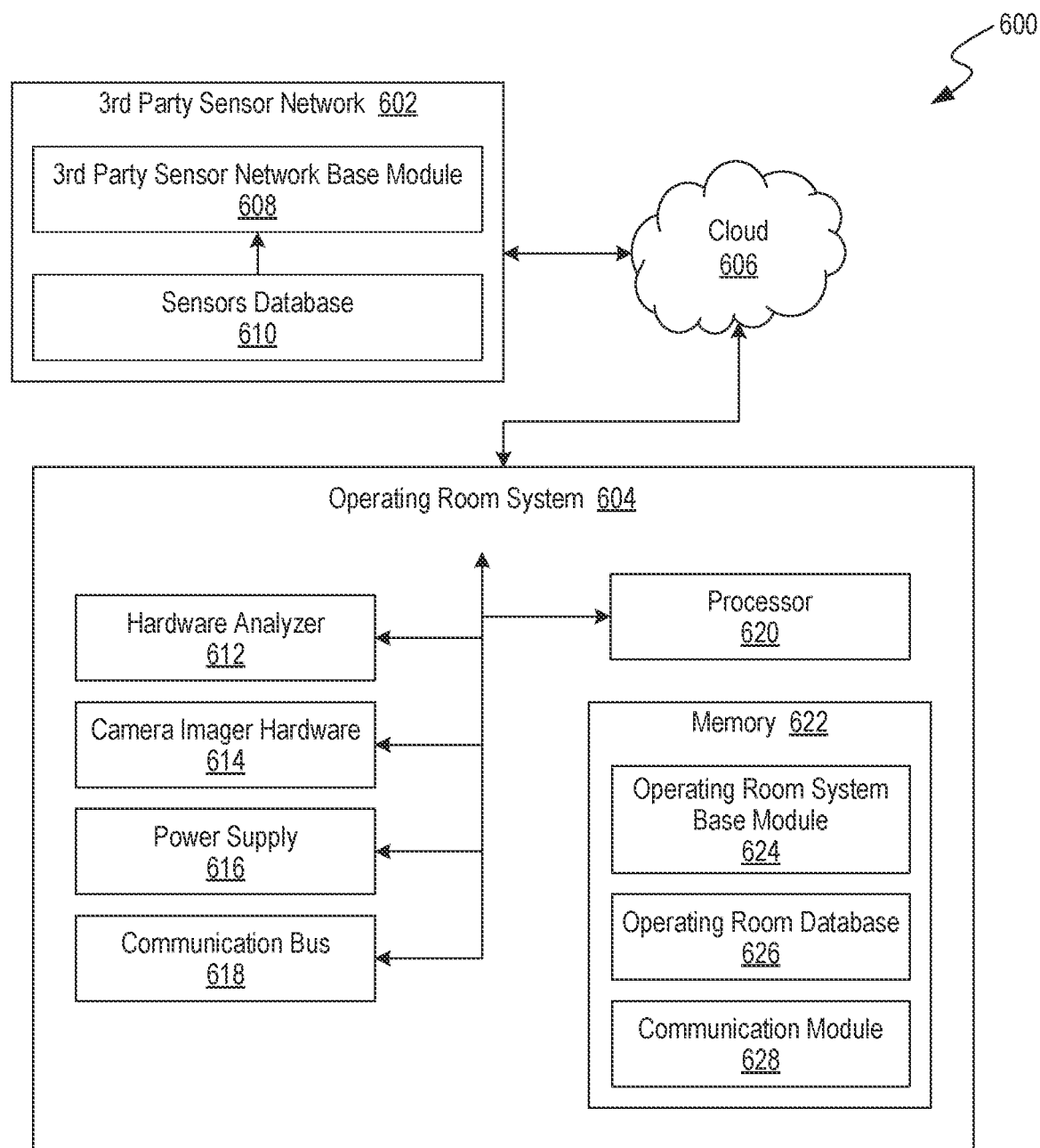
FIG. 6A is a block diagram illustrating an example system for automated disease detection using multiple-wavelength imaging, in accordance with one or more embodiments.

FIG. 6A is a block diagram illustrating an example system 600 for automated disease detection using multiple-wavelength imaging, in accordance with one or more embodiments. The system 600 can be incorporated into or used with technology discussed in connection with FIGS. 1-5. For example, one or more components of the system 600 can be incorporated into the operating room 102 discussed in connection with FIG. 1. By way of another example, a hardware analyzer 612 and/or camera imager hardware 614 of the system 600 can be part of the interface 420 discussed in connection with FIG. 4B. Output from the system 600 can be transmitted to the controller 450 in FIG. 5 and/or various other components disclosed herein. Accordingly, the system 600 can be incorporated into robotic surgery systems, or utilized to perform manual surgical procedures or to perform other procedures disclosed herein.

The system 600 generates a two-dimensional (2D) or three-dimensional (3D) map of a target region based on captured images. Output from one or more imaging devices can be overlaid onto reference or captured images. For example, a captured image can be a color image and the output of the imaging device (e.g., imaging devices 454a, 454b, camera imager hardware 614, etc.) can be colored to provide a false clear image. The modality image can be readily identifiable by a user. This allows a user to see overlaid output or analytics generated from the imaging device. In some procedures, the imaging devices scan the targeted tissue to generate a 3D image of the tissue. The output from the imaging devices can be overlaid onto a scan or base (reference) image based on the known positional information between the imaging devices. This allows the acoustic-generated image data to be keyed between images from imaging devices.

The disclosed system 600 can detect different types of wavelengths using intelligent sensors and/or a combination of discrete sensors. In embodiments, the different types of wavelengths include, but are not limited to, radio waves, microwaves, infrared, invisible, ultrasonic, X-rays, or gamma rays (see FIG. 1). Portions of the system 600 are implemented using the components of the example computer system 300 illustrated and described in more detail with reference to FIG. 3. Likewise, embodiments of the system 600 can include different and/or additional components or can be connected in different ways. In embodiments, the system 600 uses sound waves or acoustic energy (ultrasound imaging modality) in a frequency above human hearing (20,000 Hertz (Hz) or 20 kHz). A diagnostic sonographic scanner can be used in a frequency range of 2 to 18 MHz, hundreds of times greater than the limit of human hearing. In embodiments, X-ray imaging is performed using electromagnetic radiation of extremely short wavelength and high frequency, with wavelengths ranging from about $10^{-8}$ to $10^{-12}$ meters (m) and corresponding frequencies from about $10^{16}$ to $10^{20}$ Hz.

In some embodiments, the system 600 performs one or more multi-modality analyses in which one or more multi-sensing devices (e.g., multi-modality imagers, multiple imaging machines, etc.) perform (sequentially or concurrently) multiple scans/tests, such as CT scans, radiation tests, sound tests, optical tests, acoustic tests, photoacoustic tests, combinations thereof, or the like. In embodiments, a multi-modality image can simultaneously image a target region to capture images with matching perspectives relative to the target region such that features from one image can be overlayed onto another, features from multiple images can be stitched together to form a composite image, and/or cross-image features identification can be performed. In embodiments, tests are performed during one or more scans of the target region. In a single scan test, the system 600 can concurrently perform multiple tests while moving along the tissue sample. In multiple scan tests, the system 600 sequentially performs tests during corresponding scans and/or concurrently performs multiple tests during each scan. The system 600 can perform different testing, imaging, and/or scanning protocols based on the analysis to be performed.

The system 600 can facilitate communication with a robotic surgical system, doctor, surgeon, or other medical professional by providing results (e.g., multi-modality data, raw data, visualizations of the data, and the like) from the test(s) in real-time. Further, the system 600 can combine the results from imaging device(s) to provide a diagnosis of a tissue sample, target region, surgical site, or combinations thereof. In surgical procedures, the results can be automatically transmitted to a surgical robot that analyses the results to perform one or more surgical steps. The surgical robot can request additional information from the system 600 to, for example, complete a surgical step, confirm completion of a surgical step, plan a surgical step, plan a series of surgical steps, or the like. For example, the surgical system 402 at FIG. 4A can receive multi-modality results from the system 600 to perform a multi-modality-guided robotic surgical step. In embodiments, the results are displayed via display 422 for viewing by the surgical team, as shown in FIG. 4A. Features of exemplary viewable multi-modality results are discussed in connection with FIG. 15. Additionally, or alternatively, the results can be viewable via console 420 by a user 421 of FIG. 4A while, for example, monitoring or performing one or more surgical steps.

In embodiments, the system 600 captures images of a region of interest of a patient's anatomy using a first imaging device and a second imaging device. The first imaging device uses a first imaging modality and the second imaging device uses a second imaging modality. The system 600 uses the different types of detected wavelengths individually or in combination for a variety of medical and non-medical applications. In embodiments, multimodal image fusion is performed. A first set of data points and a second set of data points are fused by amalgamating two or more images from single or multiple imaging modalities, such as positron emission tomography, single photon emission computed tomography, computed tomography, or magnetic resonance imaging into a single distinct image having more-detailed anatomical and spectral information. The data points can be two-dimensional (X,Y) data points, three-dimensional data points, four-dimensional data points, etc. The benefits of the embodiments are to improve the quality of an image while preserving the most desirable and relevant characteristics of each in order to make the image more usable for clinical diagnosis and treatment procedure. In embodiments, feature processing, machine learning, and sparse representation are used to learn informative characteristics that portray the patterns and regularities in each set of data points.

In embodiments, the system 600 locates a particular tissue structure of a region of interest during a surgical procedure by a surgical robot using a fused first set of (X,Y) data points and a second set of (X,Y) data points. For example, the system 600 can use this data to locate tissue structures during a surgical procedure. In embodiments, the first set of (X,Y) data points is obtained using wavelengths of light in a visible spectrum, and a second set of (X,Y) data points includes temperatures detected via infrared (IR) imaging. A first imaging device can include a camera, an optical probe, a photodetector, etc. A second imaging device can include an IR scanner, an IR detector, an IR camera, etc.

In embodiments, the first set of (X,Y) data points is obtained using electromagnetic waves, and the second set of (X,Y) data points is obtained using sound waves. For example, the first imaging device can be an X-ray machine and the second imaging device can be an ultrasound machine. The data points used can be a combination of X-ray and ultrasound measurements used to detect a bone disease. The wavelengths correspond to operating wavelengths of analysis tools or imaging modalities, using electromagnetic or sound waves. In embodiments, the system 600 uses morphological information to locate particular tissue structures. For example, data from histological images can be used as input to generate clusters using the k-means algorithm. Loose connective tissue, light regions and cell nuclei can be located using the fused first set of (X,Y) data points and second set of (X,Y) data points. For example, tissue features, such as shape and spatial projection are used. In embodiments, the machine learning system 200 (see FIG. 2) is used along with manually annotated images that are used as a ground-truth or for ML training.

In embodiments, the system 600 employs the analysis tools or the imaging modalities to diagnose a medical condition of a patient. For example, system 600 detects a medical condition of the patient and a confidence level using the machine learning system 200 (see FIG. 2) by correlating a fused first set of (X,Y) data points and a second set of (X,Y) data points to stored patient data. For example, the correlating can include determining Pearson correlation, Kendall rank correlation, Spearman correlation, or Point-Biserial correlation between the fused first set of (X,Y) data points and second set of (X,Y) data points to the stored patient data. In embodiments, the system 600 determines a probability that a region of interest is infected (see FIG. 12) using multiple imaging modalities including a first imaging modality (e.g., visible light) and a second imaging modality (e.g., IR imaging).

The system 600 can include a third-party sensor network 602 and an operating room system 604 communicatively coupled to each other via the cloud 606 (see FIG. 3). The cloud 606 is a distributed network of computing resources. The third-party sensor network 602 includes a third-party sensor network base module 608, which can include any of an initiation module, an imager module, a reference region module, a first analyzer module and a second analyzer module, a fuser module and a display module, and a sensors database 610 to store parameters related to different imaging modalities. Further, the operating room system 604 can include a hardware analyzer 612, an imaging device in the form of the camera imager hardware 614, a power supply 616, a communication bus 618, a processor 620, and a memory 622. The memory 622 can further include an operating room system base module 624 and an operating room database 626. The third-party sensor network 602 can be directly coupled with the operating room system 604 over the cloud 606. The third-party sensor network 602 is a network of sensors connected to the system 604. In embodiments, the operating room system 604 is a medical imaging system with imaging devices that utilize electromagnetic or sound waves of varying wavelengths for an application, especially in medical surgeries.

The cloud 606 facilitates communication links among the components of the system 600. The cloud 606 can be a wired and/or a wireless network. The cloud 606, if wireless, can be implemented using communication techniques such as Visible Light Communication (VLC), Worldwide Interoperability for Microwave Access (WiMAX), Long Term Evolution (LTE), Wireless Local Area Network (WLAN), infrared (IR) communication, Public Switched Telephone Network (PSTN), radio waves, and other communication techniques known in the art (see FIG. 3).

In embodiments, the system 600 establishes communication channels between a first imaging device, a second imaging device, and the machine learning system 200 (see FIG. 2). The machine learning system 200 can be implemented on the third-party sensor network 602, the memory 622, on a cloud server, or on a surgical robot. In embodiments, the machine learning system 200 can be implemented on an imaging device. For example, the third-party sensor network base module 608 establishes communication with the operating room (OR) system 604, over the cloud 606. The communication channels can be implemented using the network adapter 312, network 314, or bus 316 in FIG. 3.

The third-party sensor network base module 608 is configured to establish an initiation procedure, or handshake procedure, with the operating room system 604 and the operating room database 626. The third-party sensor network base module 608 is configured to send the information from the sensors to the operating room system 604 from the sensors database 610. The third-party sensor network base module 608 is configured to update the sensors database 610. Further, the third-party sensor network base module 608 is configured to receive data from the operating room system 604. The third-party sensor network base module 608 is configured to send the information related to the sensors to the operating room system 604 to update the operating room database 626 in the operating room system 604. Further, the third-party sensor network base module 608 is configured to synchronize the operating room database 626 of the operating room system 604 with the sensors database 610. For instance, the third-party sensor network base module 608 ensures that the operating room database 626 is being updated with real-time data, firmware, historical data, etc.

In embodiments, the sensors database 610, as shown in FIG. 6A, is configured to store information related to multiple sensors of the operating room system 604. Further, the sensors database 610 is configured to store information related to at least two different imaging modalities. Further, the sensors database 610 stores information related to disease state data analyzed using at least two different imaging modalities. Further, the sensors database 610 is coupled with the third-party sensor network base module 608 and medical equipment of the operating room system 604 via the cloud 606. The medical equipment is illustrated and described in more detail with reference to FIG. 1.

The operating room system 604 can include hardware analyzers 612, each including an imaging modality. The hardware analyzer 612 of the operating room system 604 can include a plurality of analyzers employed individually or in combination to image a patient and analyze the collected information in real time. The hardware analyzer 612 can employ analyzers according to a targeted medical condition to be diagnosed. For example, the hardware analyzer 612 employs X-ray and ultrasound to detect osteoporosis of bone tissue. In embodiments, the plurality of analyzers includes, but is not limited to, X-ray, infrared (IR), visible light, computer tomography (CT), magnetic resonance imaging (MRI), ultrasound, and positron emission tomography (PET). In embodiments, a first set of (X,Y) data points is obtained using PET, and a second set of (X,Y) data points is fused with the first set of (X,Y) data points using a fiduciary marker. For example, medical infrared thermography (MIT) is used for analyzing physiological functions related to skin temperature. MIT is a non-invasive, non-radiating, low-cost detection tool. For example, anatomical and physiological information is determined by image fusion, which helps to localize an affected region and extent of injury of a patient. The IR images are obtained through the energy from the human tissue, leading to a classification based on the energy applied to the body. The energy content of the emission is related to the wavelength of the radiation. Human skin emits IR radiation mainly in the wavelength range of 2-20 µm with an average peak of 9-10 µm. Approximately 90% of the emitted IR radiation in a patient is of longer wavelength (8-15 µm).

In embodiments, the system 600 captures first images of the region of interest by a first imaging device of the medical equipment using a first imaging modality. The system can place a fiduciary marker in the region of interest, wherein the fiduciary marker is visible in the first images and in second images. For example, a visible light imaging modality is used, such as encapsulating color images, e.g., in JPEG format, where the images captured include specialty-specific acquisition context metadata. The visible-light imaging modality can be used by a surgical robot (see FIGS. 4A-B) for performing endoscopy (including fiberoptic endoscopy or rigid scope endoscopy), angioscopy, arthroscopy, bronchoscopy, colposcopy, etc. The visible-light imaging modality can be used by a surgical robot for performing light microscopy for anatomic pathology (e.g., transmission light microscopy and reflection light microscopy for cytology or histology), surgical microscopy (e.g., images produced by an operating microscope used in cardiothoracic surgery, neurologic surgery, ophthalmic surgery, etc.), anatomic pathology, dermatology, aesthetic (cosmetic) or reconstructive plastic surgery, etc.

In embodiments, the imaging devices use a computer tomography (CT) modality to generate a two-dimensional (2D) or three-dimensional (3D) image of the scanned region of interest. The CT images are a compilation of computer processed X-ray images taken at a range of angles around the region to produce a single cross sectional image. The region can be moved forward within the imaging device to scan a next cross section similarly. The cross sectional images can be viewed side by side or stacked on top of one another to create a 3D scan of the region. In embodiments, an imaging device uses an MRI imaging modality to provide highly detailed images of tissue structures. The imaging device detects and processes the signals generated when hydrogen atoms, which are abundant in tissue, are placed in a strong magnetic field and excited by a resonant magnetic excitation pulse. An RF receiver is used to process the signals from the receiver coils. The MRI device can have six or more receivers to process the signals from multiple coils. The signals range from approximately 1 MHz to 300 MHz, with the frequency range dependent on applied-static magnetic field strength. The bandwidth of the received signal is typically less than 20 kHz, and dependent on the magnitude of the gradient field.

In embodiments, the system 600 captures second images of the region of interest by a second imaging device of the medical equipment using a second imaging modality. The fiduciary marker is visible in the second images. In embodiments, an imaging device uses a PET imaging modality to measure metabolic activity of the cells of body tissues of the patient. The PET imaging modality provides a visualization of biochemical changes taking place in the patient's body, such as metabolism.

In embodiments, a first set of (X,Y) data points is obtained using magnetic resonance imaging (MRI), a set of second images includes brain images generated by magnetoencephalography, and fusing a second set of (X,Y) data points with the first set of (X,Y) data points provides a source of brain activity in the patient. For example, a first imaging modality is MRI, a second imaging modality is CT, and a third imaging modality is PET to provide a more definitive detection of malignant (cancerous) tumors, other lesions, Alzheimer's disease, or coronary artery disease and a higher confidence level using the machine learning system 200 (see FIG. 2) by correlating a fused first set of (X,Y) data points from PET, a second set of (X,Y) data points from CT, and a third set of (X,Y) data points from MRI to stored patient data.

The operating room system 604 can include the camera imager hardware 614 to capture images of a sample, such as bone tissue, of the patient. The camera imager hardware 614 can be an imaging device such as, but not limited to, a camera or a video recording device, with network connectivity to transmit the captured image to the operating room system 604 in real time. Further, the camera imager hardware 614 can generate a map corresponding to the captured image. In embodiments, the generated map of the captured image is aligned with images acquired using different imaging modalities.

In embodiments, the system 600 triggers the robotic surgical system to power on a first imaging device and a second imaging device using the power supply 616 of the robotic surgical system. For example, the operating room system 604 includes the power supply 616 to provide power to multiple components of the operating room system 604. The multiple components include different imaging devices within an operating room (OR) necessary to perform testing and analysis of the sample of a bone tissue or a target tissue of the patient. The power supply 616 can be configured to convert electric current from a source to a corrected voltage, current, and frequency to power multiple components of the operating room system 604. In embodiments, the power supply 616 is an internal power source to the operating room system 604. In other embodiments, the power supply 616 is an external power source to the operating room system 604. The power supply 616 can be a battery. Further, the battery can be a lithium polymer (Li—Po), lithium-ion, nickel-metal hydride, lead-acid, or ultracapacitor battery, having a lighter weight, higher discharge rate, and higher capacity.

The operating room system 604 can include the communication bus 618 to transfer information between the plurality of components within the operating room system 604. Further, the communication bus 618 can be configured to communicate data acquired via the different imaging modalities used during the medical surgery. The communication bus 618 can be, but is not limited to, an ethernet port, Wi-Fi antenna, Bluetooth transceiver, serial port, universal serial bus (USB), etc.

Further, the operating room system 604 can include the processor 620 configured to execute instructions within a program. The processor 620 can perform calculations on data acquired from the imaging modalities used in the medical surgery/surgical procedure of the patient, to determine tissue structures including cancerous tissues. Further, the processor 620 can perform analysis of image data acquired via the camera imager hardware 614 to create a map for alignment with data acquired by the different imaging modalities.

Further, the operating room system 604 can include the memory 622 communicatively coupled to the third-party sensor network 602 and the operating room system 604 over the cloud 606. The memory 622 can be communicatively coupled to the hardware analyzer 612, the camera imager hardware 614, the power supply 616, the communication bus 618, and the processor 620 of the operating room system 604. In embodiments, the system 600 of FIG. 6A identifies tissue structures of the region of interest using image processing performed on first images and second images by referencing a fiduciary marker. The first images are captured using a first imaging modality and the second images are captured using a second imaging modality. For example, the memory 622 can store the information related to the imaging modalities used in the surgical procedure, in order to identify tissue structures. Further, the memory 622 can store information acquired via the different imaging modalities used during the medical surgery. Further, the memory 622 can store information related to the map corresponding to the captured image of the patient and the different image modalities. The system 600 can perform automated tissue image analysis or histopathology image analysis (HIMA) using image processing to identify tissue structures, e.g., using computations to derive quantitative measurements from images to avoid subjective errors.

Further, the memory 622 can include the operating room system base module 624, the operating room database 626, and a communication module 628. The operating room system base module 624 can communicate with third-party vendors to get information, firmware, or software related to the hardware analyzers, such as X-ray, ultrasound, etc. Further, the operating room system base module 624 can receive real-time sensor data from the hardware analyzer 612.

The operating room database 626 can store data related to an ongoing surgical procedure. In embodiments, the real-time data includes, but is not limited to, heart rate, blood oxygen saturation (SpO2), respiration rate, and blood pressure. Further, the operating room database 626 also stores information related to staff within the OR. The information related to staff includes, but is not limited to, information about surgeons, nurses, anesthesiologists, etc. Further, the operating room database 626 stores information related to the medical devices and equipment used. For example, the operating room database 626 stores the vital signs of patient Alex including a heart rate of 82, SpO2 of 98, and blood pressure of 120/85.

Further, the operating room system base module 624 can include the communication module 628 to establish and maintain communication between the operating room system 604 with the third-party sensor network 602 and the cloud 606. The operation of the communication module 628 is described in more detail with reference to FIG. 6B and FIG. 7.

Figure 6B:
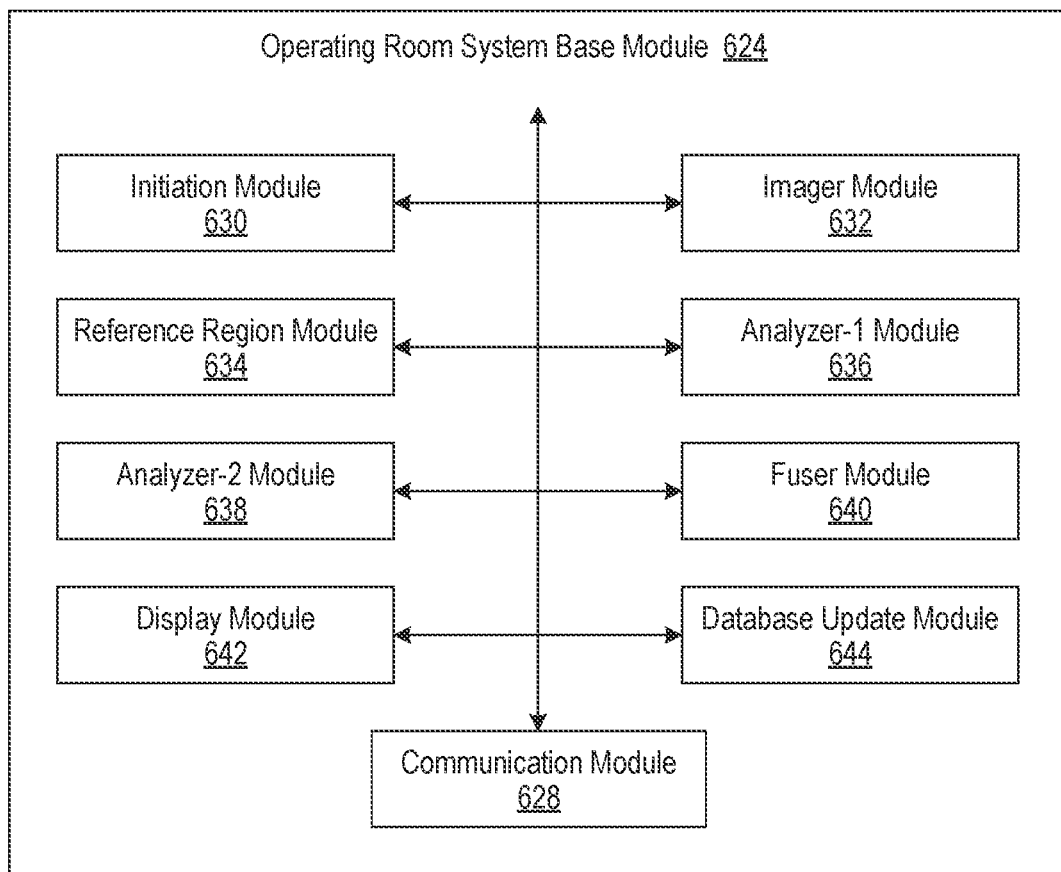
FIG. 6B is a block diagram illustrating an example operating room system base module for automated disease detection using multiple-wavelength imaging, in accordance with one or more embodiments.

FIG. 6B is a block diagram illustrating an example operating room system base module 624 for automated disease detection using multiple-wavelength imaging, in accordance with one or more embodiments. The operating room system base module 624 includes multiple sub-modules to carry out operations related to correlating data acquired using multiple imaging modalities and detecting a range of electromagnetic or sound wavelengths. The imaging modalities can be state-of-the-art imaging modalities, without departing from the scope of the disclosure. In embodiments, the system 600 places a fiduciary marker in a region of interest of a patient's anatomy. Fiduciary markers are used to correlate images of the same patient produced using different imaging modalities (sometimes called image registration). A fiduciary marker is placed in a region of interest imaged by different modalities. A marker which is visible in the images produced by different imaging modalities is used. In embodiments, a first set of (X,Y) data points is obtained using magnetic resonance imaging (MRI). Captured second images include brain images generated by magnetoencephalography. Fusing the first set of (X,Y) data points with a second set of (X,Y) data points obtained from the second images provides a source of brain activity in the patient. For example, functional information from SPECT or positron emission tomography can be related to anatomical information provided by magnetic resonance imaging (MRI). Similarly, fiducial points established during MRI can be correlated with brain images generated by magnetoencephalography to localize the source of brain activity.

The operating room system base module 624 includes the communication module 628, an initiation module 630, an imager module 632, a reference region module 634, a first analyzer module 636, a second analyzer module 638, a fuser module 640, a display module 642, and a database update module 644. In embodiments, the system 600 fuses the first set of (X,Y) data points and the second set of (X,Y) data points (including data points from any other imaging modalities used). For example, HSL (hue, saturation, lightness) or HSV (hue, saturation, value) transform-based fusion, principal component analysis (PCA)-based fusion, wavelet transform fusion, pair-wise spatial frequency matching, another fusion method, or a combination thereof can be used. For example, in step 712, the operating room system base module 624 triggers the fuser module 640 to combine and compare data from the first analyzer module 636 and the second analyzer module 638. In embodiments, the measurements derived from the disparate imaging modalities are fused, such that the resulting information has less uncertainty than would be possible when these modalities are used individually.

The communication module 628 can retrieve data from the cloud 606 or the sensors database 610 of the third-party sensor network 602 to provide data in addition to the data acquired by the hardware analyzers 612 and the camera imager hardware 614. The communication module 628 can enable the operating room system base module 624 to send the image data obtained from the imager module 632, the first analyzer module 636, the second analyzer module 638, and the fused image data, to the cloud 606 or the sensors database 610 of the third-party sensor network 602 to be stored there for future reference. The communication module 628 can be used by the database update module 644 to send data relating to the current patient or procedure, as acquired from the hardware analyzers 612, to the operating room database 626, the sensors database 610 of the third-party sensor network 602, or the cloud 606.

Figure 7:
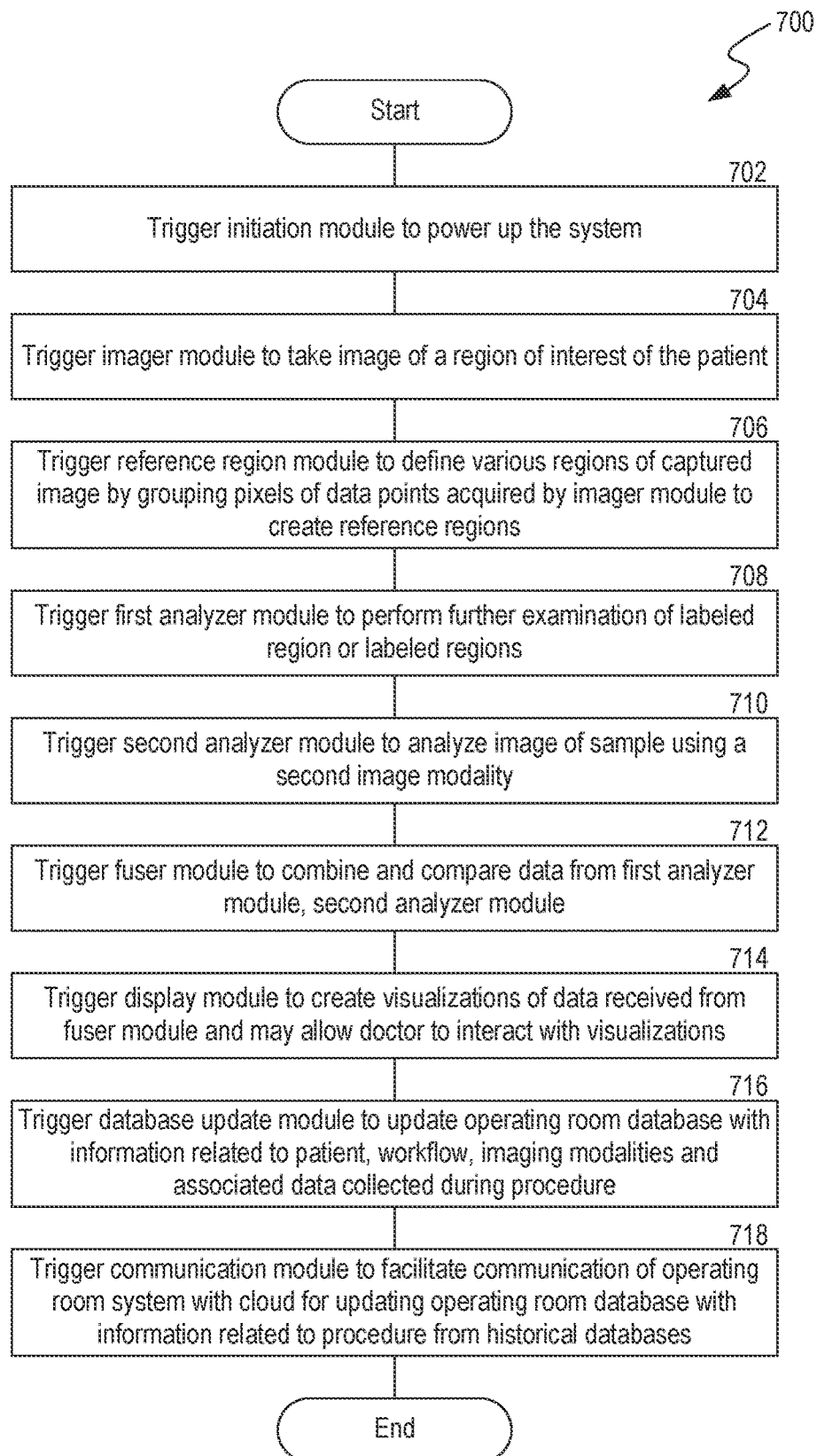
FIG. 7 is a flow diagram illustrating an example process for automated disease detection using multiple-wavelength imaging, in accordance with one or more embodiments.

FIG. 7 is a flow diagram illustrating an example process 700 for automated disease detection using multiple-wavelength imaging, in accordance with one or more embodiments. An example operating room 102 is illustrated and described in more detail with reference to FIG. 1. In some embodiments, the process 700 of FIG. 7 is performed by the operating room system base module 624. The operating room system base module 624 is illustrated and described in more detail with reference to FIGS. 6A and 6B. In other embodiments, the process 700 of FIG. 7 is performed by a computer system, e.g., the example computer system 300 illustrated and described in more detail with reference to FIG. 3. Particular entities, for example, the console 108 or the robotic surgical system 160 perform some or all of the steps of the process 700 in other embodiments. The console 108 and the robotic surgical system 160 are illustrated and described in more detail with reference to FIG. 1. Likewise, embodiments can include different and/or additional steps, or perform the steps in different orders.

In embodiments, the system 600 triggers the robotic surgical system to power on a first imaging device and a second imaging device using the power supply 616 of the robotic surgical system. For example, the operating room system 604 includes the power supply 616 to provide power to multiple components of the operating room system 604. The multiple components include different imaging devices within an operating room (OR) necessary to perform testing and analysis of the sample of a bone tissue or a target tissue of the patient. For example, in step 702, the operating room system base module 624 triggers the initiation module 630 to power up the system 600. The initiation module 630 turns on the system 600 and the medical equipment of the operating room system 604. In embodiments, the initiation module 630 turns on or powers on the medical equipment.

The power can be provided by the power supply 616. The power supply 616 is an electrical device that supplies electric power to the medical equipment (see FIG. 1). The power supply 616 converts electric current from a source to the correct voltage, current, and frequency to power the load of each imaging device. In embodiments, the system 600 verifies operability of medical equipment of a robotic surgical system. For example, the initiation module 630 can be configured to verify the operability of the medical equipment of the operating room system 604. The medical equipment of the operating room system 604 can be part of a robotic surgical system (see FIGS. 4A-B).

The initiation module 630 can be configured to establish communication between units of the medical equipment of the operating room system 604. The step of establishing communication can include an initiation procedure, or handshake, between imaging devices such that a request is sent from a first imaging device to a second imaging device, which then sends a response to the first imaging device confirming that the first and second imaging devices are communicating via the established connection. The handshake procedure can include a process that establishes communication between two networking devices of the medical equipment. For example, when two imaging devices first connect with each other through modems or other devices, the handshaking process determines which protocols, speeds, compression, and error-correction schemes will be used during the communication session.

In embodiments, the system 600 verifies operability of medical equipment of a robotic surgical system. For example, the initiation module 630 can be configured to verify the operability of the medical equipment of the operating room system 604. The medical equipment of the operating room system 604 can be part of a robotic surgical system (see FIGS. 4A-B). The operability can be verified by acquiring test patterns (data from a sample for which the expected results are known) and comparing the acquired data with the expected values. The test patterns can be digital data, analog data, or a combination thereof. The medical equipment is operational if the acquired data matches the expected results within a predetermined threshold value or tolerance. In embodiments, the initiation module 630 verifies the operability of the medical equipment using self-tests to discover a imaging device needs maintenance or repair. The test patterns can be for temperature, humidity, faulty communications, or a bad connection to a power supply. Communication tests can be performed by verifying the presence of periodic test patterns called frames. For example, frames can repeat about 8,000 times per second.

In addition, the initiation module 630 can be configured to verify the operability of the medical equipment of the operating room system 604 using test patterns to loop-back the communications locally, to test a transmitter and a receiver, and remotely, to test the communications link without using the computer or software at the imaging device. Where electronic loop-backs are absent, the software usually provides the test patterns. For example, IP defines a local address which is a software loopback (IP Address 127.0.0.1, usually locally mapped to name "localhost"). Each imaging device can also have an automatic reset feature to restart the remote functionality. The rest can be triggered by lack of communications, improper software operation, or other critical events. Each imaging device can further test itself to assure its continued safety. For example, a power-on self-test (POST) performs a more comprehensive test. Second, a periodic test determines that the imaging device has not become unsafe since the power-on self-test.

Safety-critical medical equipment can define a "safety interval," a period of time too short for injury to a patient to occur. The self-test of the more critical functions normally is completed at least once per safety interval. The periodic test is normally a subset of the power-on self-test.

In step 704, the operating room system base module 624 triggers the imager module 632 to take images of a region of interest of the patient's anatomy. A "region of interest" or "region" is a portion of the anatomy, e.g., head, neck, thorax, abdomen, pelvis, or upper or lower extremities. An upper limb can further be divided into regions, such as shoulder, arm, elbow, forearm, wrist, or hand. In embodiments, the system 600 places a fiduciary marker in a region of interest of a patient's anatomy. Fiduciary markers are used to correlate images of the same patient produced using different imaging modalities (sometimes called image registration).

In embodiments, the system 600 verifies operability of medical equipment of a robotic surgical system by, for example, performing an operability protocol on the medical equipment to determine a state of operation (e.g., ON state, OFF state, SLEEP mode), or imaging capability of the medical equipment, etc. The medical equipment includes a first imaging device and a second imaging device. The system 600 captures first images of the region of interest by the first imaging device using a first imaging modality. The fiduciary marker is visible in the first images. For example, the imager module 632 boots up the camera imager hardware 614 (first imaging device), providing power and allowing the camera imager hardware 614 to initialize, perform self-test, verify the camera imager hardware 614's operability, and perform any required software or hardware checks to ensure proper operation. The imager module 632 then takes an image of the region of interest using the camera imager hardware 614 (the first imaging modality is visible light imaging). For example, the imager module 632 uses the camera of the camera imager hardware 614 to take a picture of a patient's right leg. Further, the captured image can be stored in the operating room database 626.

In embodiments, the system 600 determines a first set of (X,Y) data points describing tissue structures of the region of interest using first images (captured using a first imaging modality) and a second set of (X,Y) data points describing the tissue structures using second images (captured using a second imaging modality). For example, the imager module 632 can convert data within the captured image to a set of (X,Y) data points. In embodiments, the first set of (X,Y) data points is obtained using wavelengths of light in a visible spectrum, and a second set of (X,Y) data points include temperatures detected via infrared (IR) imaging. A first imaging device can include a camera, an optical probe, a photodetector, etc. A second imaging device can include an IR scanner, an IR detector, an IR camera, etc. In embodiments, the (X,Y) data points correspond to pixel-by-pixel grid color code values. The grid color code values can include, but are not limited to, red, green, blue (RGB) values. The pixel-by-pixel grid RGB values of the first set of (X,Y) data points can be converted to gray scale such that each point of the captured image represents an intensity of light received by the camera imager hardware 614. Further, the imager module 632 can save the set of (X,Y) data points to the operating room database 626. The set of (X,Y) data points may be updated to the operating room database 626 in real time.

In embodiments, the system 600 generates a map from captured images by grouping pixels of the images and determining segments of the images using the machine learning system 200 (see FIG. 2) based on the grouping to provide the map. For example, in step 706, the operating room system base module 624 triggers the reference region module 634 to define various segments of the captured image by grouping the pixels of the (X,Y) data points acquired by the imager module 632 to create reference segments. The reference region module 634 generates a map using the first set of (X,Y) data points. Edge detection, artificial intelligence, and/or machine learning techniques (see FIG. 2) are used to identify reference segments and plot them on the generated map. The (X,Y) data points can represent Cartesian coordinates along an X-axis and a Y-axis. The reference segments can be analyzed by the doctor, to ensure the correctness of the various segments. The reference segments of the captured image can be displayed via a user interface (see FIG. 3). In embodiments, the user interface includes, but is not limited to, a computer, a portable smart screen, and a mobile smart screen.

In embodiments, the ML system 200 illustrated and described in more detail with reference to FIG. 2 extracts features from the images and uses a combination of digital image processing, computer vision, and image segmentation to partition an image into multiple image segments, also known as image regions or image objects (sets of pixels). The embodiments simplify and/or change the representation of the image into segments that are more meaningful and easier to analyze. The methods disclosed herein can be used to locate objects and boundaries (lines, curves, etc.) in images. The methods can assign a label to each pixel in an image such that pixels with the same label share certain characteristics. In embodiments, the set of segments generated cover the entire image, or at least a set of contours extracted from the image. Each of the pixels in a segment can be similar with respect to some characteristic or computed property, such as color, intensity, or texture. Adjacent segments are different with respect to the same characteristic(s). When applied to a stack of images in medical imaging, the resulting contours after the image segmentation can be used to create two-dimensional (2D) or three-dimensional (3D) reconstructions with the help of interpolation algorithms, such as marching cubes.

In embodiments, the reference region module 634 improves in identifying the image segments over time. The reference region module 634 can detect edges of the sample from the reference segment. For example, the reference region module 634 identifies edges from a captured image, Picture 1, defining bone tissue, as the reference segments using the ML system 200. In embodiments, edges can even be manually identified by a doctor over the user interface. For example, the reference region module 634 identifies edges defined by a contrast in the magnitude of light of gray-scale images. Successively, the reference region module 634 can label a segment enclosed by the identified edges by comparing the detected images to similar previously acquired images. For example, the reference region module 634 labels a segment bound by the detected edges by comparing the image with a database of similar images, and determining the segment that constitutes bone tissue. The segment can further be identified as a specific structure, such as the femur of a patient's right leg.

The reference region module 634 can convert the labeled segment or labeled segments to a second set of (X,Y) data points. In embodiments, the reference region module 634 uses edge detection to identify tissue structures, such as bones, ligaments, organs, etc., which are then used to align data acquired by the analyzer modules. The reference region module 634 can save data related to the labeled segment to the operating room database 626. For example, the reference region module 634 saves the second set of data of an image map extracted from the camera files to the operating room database 626.

In step 708, the operating room system base module 624 triggers the first analyzer module 636 to perform further examination of the labeled segment or the labeled segments. The first analyzer module 636 can turn on hardware, such as an X-ray machine corresponding with a first imaging modality. In embodiments, the first imaging modality is an X-ray. In other embodiments, the first image modality is an X-ray device or X-ray scanner to scan the labeled region/regions of the sample. The first analyzer module 636 can capture the image using the first image modality. For example, the first analyzer module 636 captures an X-ray image represented as Picture 2 of the labeled region bone tissue using the X-ray device. Further, the first analyzer module 636 can convert the image captured using the first image modality to a third set of (X,Y) data points. In embodiments, the third set of (X,Y) data points corresponds to the density of the tissues in the image, including bone density.

In embodiments, the system 600 of FIG. 6A identifies tissue structures of the region of interest using image processing performed on first images and second images by referencing a fiduciary marker. The first images are captured using a first imaging modality and the second images are captured using a second imaging modality. For example, the memory 622 can store the information related to the imaging modalities used in the surgical procedure, in order to identify tissue structures. Further, the memory 622 can store information acquired via the different imaging modalities used during the medical surgery. Further, the memory 622 can store information related to a map corresponding to the captured image of the patient and the different image modalities. The system 600 can perform automated tissue image analysis or histopathology image analysis (HIMA) using image processing to identify tissue structures, e.g., using computations to derive quantitative measurements from images to avoid subjective errors.

In embodiments, the system 600 detects a medical condition of the patient and a confidence level using the machine learning system 200 (see FIG. 2) by correlating a fused first set of (X,Y) data points and a second set of (X,Y) data points to stored patient data. For example, the first analyzer module 636 can process a radiographic image including a map of X-rays that have either passed freely through the body or have been variably attenuated (absorbed or scattered) by anatomical structures. The denser the tissue, the more the X-rays are attenuated. For example, X-rays are attenuated more by bone than by lung tissue. The stored patient data includes portions of the data illustrated in FIG. 8A, FIG. 8B, FIG. 10, FIG. 11, FIG. 12, FIG. 13, FIG. 14, EMR data (see FIG. 1), or a combination thereof.

The first analyzer module 636 determines a contrast within the image segment based on differences in the density of structures in the body or the thickness of those structures. The greater the difference in either density or thickness of two adjacent structures leads to greater contrast between those structures within the segment. In embodiments, multiple different reference densities (air, fat, soft tissue, bone, or metal) are used to determine the nature of an abnormality or medical condition. If there is an unexpected increase or decrease in the density of a known anatomical structure, this enables the first analyzer module 636 to detect a tissue structure of the abnormality.

The feature extraction module 208 (see FIG. 2) can extract features 212 from a fused first set of (X,Y) data points and a second set of (X,Y) data points. The features 212 indicate a likelihood of a particular condition. In embodiments using a CNN, only implicit feature extraction is performed by the ML model 216 itself. The ML output 224 indicates the medical condition and a confidence level that the output 224 is correct. The confidence level can be a score from 0-1, e.g., 0.75, or a number between 0-100, e.g., 84, etc. The training data 220 can include historical patient data, patient data specific to a patient, historical surgical records, or electronic medical records (see FIG. 1).

In embodiments, the first analyzer module 636 converts the third set of (X,Y) data points to a probability of a medical condition. The medical condition can be, but is not limited to, osteoporosis. In embodiments, the first analyzer module 636 detects a reduction in bone mass or a degradation of the microarchitecture of bone tissue by extracting morphological information enabling the description of bone structure from radiological images of the calcaneus. For example, the first analyzer module 636 uses bone descriptors similar to classical two-dimensional (2D) or three-dimensional (3D) morphological bone parameters. In embodiments, the first analyzer module 636 extracts a grayscale skeleton of the microstructures contained in the underlying segments. The resulting skeleton provides discriminant features between osteoporotic patients and control patients.

In embodiments, the ML system 200 identifies low bone mineral density and micro-architectural deterioration of bone tissue from the segments. Features such as age, sex, height, or weight of a patient can be extracted and stored for evaluation with the ML model 216 (see FIG. 2) using a 10-fold cross validation method. For example, the first analyzer module 636 converts the third data set (11, 13) into a probable condition of 0.7, which is within the threshold range of 0.6-1.0 for diagnosing osteoporosis. The first analyzer module 636 saves the medical condition corresponding to the third set of (X,Y) data points of the captured image of the sample, to the operating room database 626. For example, the first analyzer module 636 updates the operating room database 626 with the probable condition of 0.7 for diagnosing osteoporosis corresponding to the third data set of (11, 13).

In embodiments, the first analyzer module 636 evaluates the X-ray image pixel by pixel to determine bone density. For example, the X-ray image captured by the first imaging modality shows a numerical value representing the intensity of brightness such as a white color spot or a dark color spot over captured Picture 2 of the bone tissue within Picture 3, and the dark color spot corresponds to osteoporosis and the white color spot corresponds to normal bone tissue. In one case, if Picture 2 reveals a region of pixels with a high brightness visible to the doctor as a white spot, the doctor can assess that the bone tissue is densely structured and likely healthy. For example, Picture 2 reveals a region of brightness of 100 candela per square feet, indicating healthy bone. In another case, if Picture 2 reveals a region of pixels with a low brightness visible to the doctor as a dark region, the doctor can diagnose the bone tissue as having a porous structure, which can be indicative of osteoporosis. For example, Picture 2 reveals a region of brightness of 50 candela per square feet, indicating osteoporosis. Further, the acquired data can be compared to previous images to determine the probabilities of osteoporosis. A higher intensity of brightness corresponds to a healthy bone. A low intensity of brightness corresponds to a lower magnitude, indicating tissues that are not bone, or bone tissues with osteoporosis.

In embodiments, the system 600 captures second images of the region of interest by a second imaging device of the medical equipment using a second imaging modality. A fiduciary marker is visible in the second images. For example, in step 710, the operating room system base module 624 triggers the second analyzer module 638 to analyze the image segment of the sample using a second image modality. The second analyzer module 638 can analyze an image of the sample using the second image modality. In embodiments, the second image modality includes an ultrasound machine/device. First, the second analyzer module 638 can turn on a hardware, such as an X-ray machine. Further, the second analyzer module 638 can capture the image using the second image modality. For example, the second analyzer module 638 captures an image of the bone tissue using the ultrasound device and assigns the image as Picture 3. Further, the second analyzer module 638 can convert the image captured using the second image modality to a CSV file with image file names. A fourth set of (X,Y) data points generated by the second image modality can correspond to the bone density of the sample. For example, the second analyzer module 638 converts data within Picture 3 into a CSV file with image file names. The bone density can be extracted as a feature 212a (see FIG. 2) by the ML system 200.

Further, the second analyzer module 638 can determine a probability of a medical condition from the fourth set of (X,Y) data points. The medical condition can be, but is not limited to, osteoporosis. For example, the second analyzer module 638 converts the CSV file with image names for diagnosing osteoporosis. Further, the second analyzer module 638 can save the medical condition corresponding to the fourth set of image file names of the captured image of the sample to the operating room database 626. For example, the second analyzer module 638 updates the operating room database 626 with the probable condition of 0.8 for diagnosing osteoporosis corresponding to the fourth data set of image file names.

In embodiments, the system 600 fuses the first set of (X,Y) data points and the second set of (X,Y) data points (including data points from any other imaging modalities used). For example, HSL (hue, saturation, lightness) or HSV (hue, saturation, value) transform-based fusion, principal component analysis (PCA)-based fusion, wavelet transform fusion, pair-wise spatial frequency matching, another fusion method, or a combination thereof can be used. For example, in step 712, the operating room system base module 624 triggers the fuser module 640 to combine and compare data from the first analyzer module 636 and the second analyzer module 638. In embodiments, the measurements derived from the disparate imaging modalities are fused, such that the resulting information has less uncertainty than would be possible when these modalities are used individually. For example, a-more accurate location estimate of errant tissue can be obtained by combining multiple modality data sources. In embodiments, a more-complete anatomical model results, such as from stereoscopic vision (calculation of depth information by combining two-dimensional images from two modalities at different viewpoints). In a first embodiments, direct fusion is performed, which is the fusion of measurements from a set of heterogeneous or homogeneous modalities. In a second embodiment, indirect fusion uses information sources such as a priori knowledge about the anatomy and human input.

The fuser module 640 can align and compare the data related to the captured images from the imager module 632, the first analyzer module 636, and the second analyzer module 638 to produce correlations using the tissue structures identified by the reference region module 634. In embodiments, the fuser module 640 receives data related to the captured images of the sample from the first analyzer module 636 and the second analyzer module 638. For example, the fuser module 640 receives Picture 2 and Picture 3 of the bone tissue from the first analyzer module 636 and the second analyzer module 638, respectively.

The fuser module 640 overlays coordinates of a third set of (X,Y) data points and a fourth set of (X,Y) data points of the captured image from the first analyzer module 636 and the second analyzer module 638 using tissue structures identified by the reference region module 634. The reference region module 634 is used to analyze data from the first analyzer module 636 and the second analyzer module 638 to similarly identify tissue structures using edge detection and similar methods. Two-dimensional (2D) or three-dimensional (3D) shapes can outline tissues in the images captured by the imager module 632, the first analyzer module 636, and the second analyzer module 638 to define regions defined by a type of tissue such as defined by 2D or 3D shapes. For example, the fuser module 640 aligns the images of Picture 2 and Picture 3 based on 2D or 3D shapes of tissue types of Picture 2 and Picture 3.

In embodiments, the captured images include first images having a first resolution and second images having a second resolution different from the first resolution. The system 600 scales the first images and the second images to a third resolution by performing convolution on the first images and the second images. For example, the fuser module 640 can scale the resolution of the captured images from the imager module 632, the first analyzer module 636, and the second analyzer module 638 to a standard resolution. In embodiments, the fuser module 640 scales the data related to the captured images to a common scale or resolution. The scaling of the data related to captured images can be achieved by a principle of convolution, to average the data of the captured images to the common resolution. In one exemplary embodiment, the fuser module 640 scales an image 1 with a first resolution to match an fiducial. In another exemplary embodiment, the fuser module 640 scales image 1 with a size 5 cm side based on relative sizes of the structures identified by the reference region module 634 of image 2 with a size 10 cm side. Successively, the fuser module 640 can analyze the data of the captured images to generate a combined probability number. In embodiments, the combined probability number is an average probability calculated for values associated with pixels corresponding to the same point across each image. Alternatively, the calculated values can be averaged within a region of interest consisting of a group of pixels. In other embodiments, the combined probability number is evaluated using artificial intelligence and/or machine learning (see FIG. 2). For example, based on the past data of patient 1, artificial intelligence and/or machine learning correlates data from the past data, i.e., correlates image 1 with image 2, to determine that patient 1 has osteoporosis.

Further, the fuser module 640 can determine whether the data is sufficient to produce a diagnosis with high confidence. In embodiments, the fuser module 640 uses prediction intervals to predict ranges in which the individual diagnoses should fall. In embodiments, the fuser module 640 uses confidence intervals to determine likely ranges of values associated with statistical parameters of the physical characteristics, such as the population mean. In one case, the fuser module 640 determines that the data analyzed from the captured images is inconclusive due to low confidence. In embodiments, the fuser module 640 calculates a standard deviation. For example, the fuser module 640 determines from Picture 1 that the bone tissue has a 0.2 probability of having osteoporosis, from Picture 2 that the probability is 0.7, and from Picture 3 that the probability is 0.5, which gives a combined probability number of 0.45 and a standard deviation of 0.3. Therefore, the doctor concludes with low confidence that the bone tissue does not have osteoporosis. In this case, the fuser module 640 can request additional information related to the images captured from the first analyzer module 636 and the second analyzer module 638. For example, the fuser module 640 requests the first analyzer module 636 to capture additional pictures of the bone tissue.

In another case, the fuser module 640 determines that the data analyzed from captured images is sufficient to diagnose the patient with high confidence. For example, the fuser module 640 determines from Picture 1 that the bone tissue has a 0.8 probability of having osteoporosis, from Picture 2 that the probability is 0.8, and from Picture 3 that the probability is 0.8, which gives a combined probability number of 0.8. This number is within a threshold combined probability number of 0.8-1.0, and therefore, the doctor concludes with high confidence that the bone tissue has osteoporosis.

In embodiments, the system 600 generates graphical visualizations of the fused first set of (X,Y) data points and the second set of (X,Y) data points for use by a physician participating in the surgical procedure with the surgical robot. Graphical visualizations are described in more detail with reference to FIG. 1. For example, in step 714, the operating room system base module 624 triggers the display module 642 to create visualizations of the data received from the fuser module 640 and allows the doctor to interact with the visualizations. The display module 642 can include a display interface through which the doctor interacts with the visualizations. The display interface can include, but is not limited to, a video monitoring display, a smartphone, a tablet, etc., (see FIG. 3).

Further, the display module 642 can convert the data related to the captured images, from the fuser module 640, into an image to display for the doctor. In embodiments, the display module 642 creates a new image in which probability values are converted to pixel values. In other embodiments, high probabilities of osteoporosis are indicated by various shades of red, with more intense reds indicating a stronger confidence. Further, low probabilities can be indicated by green, with more intense greens indicating stronger confidence that the bone density is healthy. Further, gray values can indicate that there is insufficient data. Further, the display module 642 can add a color map to the converted image. In embodiments, the color map includes, but is not limited to, the color-coding of the image file names from the first analyzer module 636 and image file names from the second analyzer module 638. For example, the display module 642 adds a map with a mixture of blue color and red color for Picture 3 and for Picture 4 which corresponds to osteoporosis, at a top side of Picture 4 of the bone tissue, so that the doctor sees the bone tissue along with osteoporosis data to conclude a diagnosis. In embodiments, the red color assigned to the map means number 10, which specifies no osteoporosis, and the white color means an algorithm with an average of 1, which specifies osteoporosis, or a colored map.

In step 716, the operating room system base module 624 triggers the database update module 644 to update the operating room database 626 with information related to patient, workflow, imaging modalities, and associated data collected during the procedure. The database update module 644 can save the information related to the patient, workflow procedure, optical, X-ray, ultrasound, hardware data, and other data collected during the workflow to the operating room database 626. For example, the database update module 644 updates the operating room database 626 with the optical data associated with Picture 1 and X-ray data associated with Picture 2.

In embodiments, the system 600 updates a surgical robot (see FIGS. 4A-B) with the fused first set of (X,Y) data points and the second set of (X,Y) data points responsive to the confidence level exceeding a threshold. In embodiments, the database update module 644 performs the updating. The updating is for a surgical procedure to be performed on the region of interest by the surgical robot for treating the medical condition. For example, the surgical robot can be updated by wireless or wire transfer of code, or by a software or firmware update. In embodiments, an ML model stored on the 602, the 622, or on a cloud server is updated by ML training (see FIG. 2) and transferred to the surgical robot. In embodiments that use edge computing, an ML model stored on the surgical robot itself is updated by ML training.

In step 718, the operating room system base module 624 triggers the communication module 628 to facilitate communication of the operating room system 604 with the cloud 606 for updating the operating room database 626 with information related to the procedure from historical databases. The communication module 628 can retrieve data from the sensors database 610 of the third-party sensor network 602, over the cloud 606, to provide data in addition to the data acquired by the hardware analyzers 612 and the camera imager hardware 614. The communication module 628 can enable the operating room system base module 624 to send the image data obtained from the imager module 632, the first analyzer module 636, the second analyzer module 638, and the fused image data, to the cloud 606 or the sensors database 610 of the third-party sensor network 602 to be stored there for future reference. The communication module 628 can be used by the database update module 644 to send data about the current patient or procedure, as acquired from the hardware analyzers 612, to the operating room database 626, the sensors database 610 of the third-party sensor network 602, or the cloud 606.

In additional embodiments, the system 600 (see description with reference to FIG. 6A) analyzes a surgical plan (see description with reference to FIGS. 4A-4B) to identify potential one or more anatomical features of interest. An anatomical feature refers to a part of or a characteristic of the structure of a patient's body, e.g., notches, nodules, or creases in the ear structure, etc. The system selects imaging modalities based on the potential one or more anatomical features of interest and available imaging modalities. The system obtains at least one image for each imaging modality and generates a multi-modality image based on each of the obtained images. In embodiments, the system determines one or more imaging characteristics for each anatomical feature of interest. The system 6060 correlates (see description with reference to FIG. 6A) the one or more imaging characteristics to identify the available imaging modalities used to select the image modalities. In embodiments, the system 600 analyzes available patient images to identify multiple patient images for a multi-modality image analysis. The system 600 determines at least one additional image modality for enabling completion of the multi-modality image analysis. The system 600 captures one or more additional images using the additional image modality. The system 600 performs the multi-modality image analysis using the multiple patient images and the captured one or more additional images.

In embodiments, the system 600 controls one or more imaging devices (see description with reference to FIG. 6A) to capture the one or more additional images with anatomical features corresponding to the anatomical features in the multiple patient images. In embodiments, the system 600 determines imaging parameters for one or more imaging devices such that the at least one additional image and one or more images in the multiple patient images have matching perspectives relative to a region of interest. For each imaging modality, the system 600 can determine one or more feature types identifiable using the image modality. The system 600 analyzes at least one image captured using the imaging modality to identify at least one feature of interest according to the feature type.

FIG. 8A illustrates a structure of an example database 626 for automated disease detection using multiple-wavelength imaging, in accordance with one or more embodiments. FIG. 8B illustrates a structure of an example database 610 for automated disease detection using multiple-wavelength imaging, in accordance with one or more embodiments. In embodiments, the system 600 determines, from captured images of a patient's anatomy, a first set of (X,Y) data points describing tissue structures of the region of interest using a first imaging modality, and a second set of (X,Y) data points describing the tissue structures using a second imaging modality.

Figure 9:
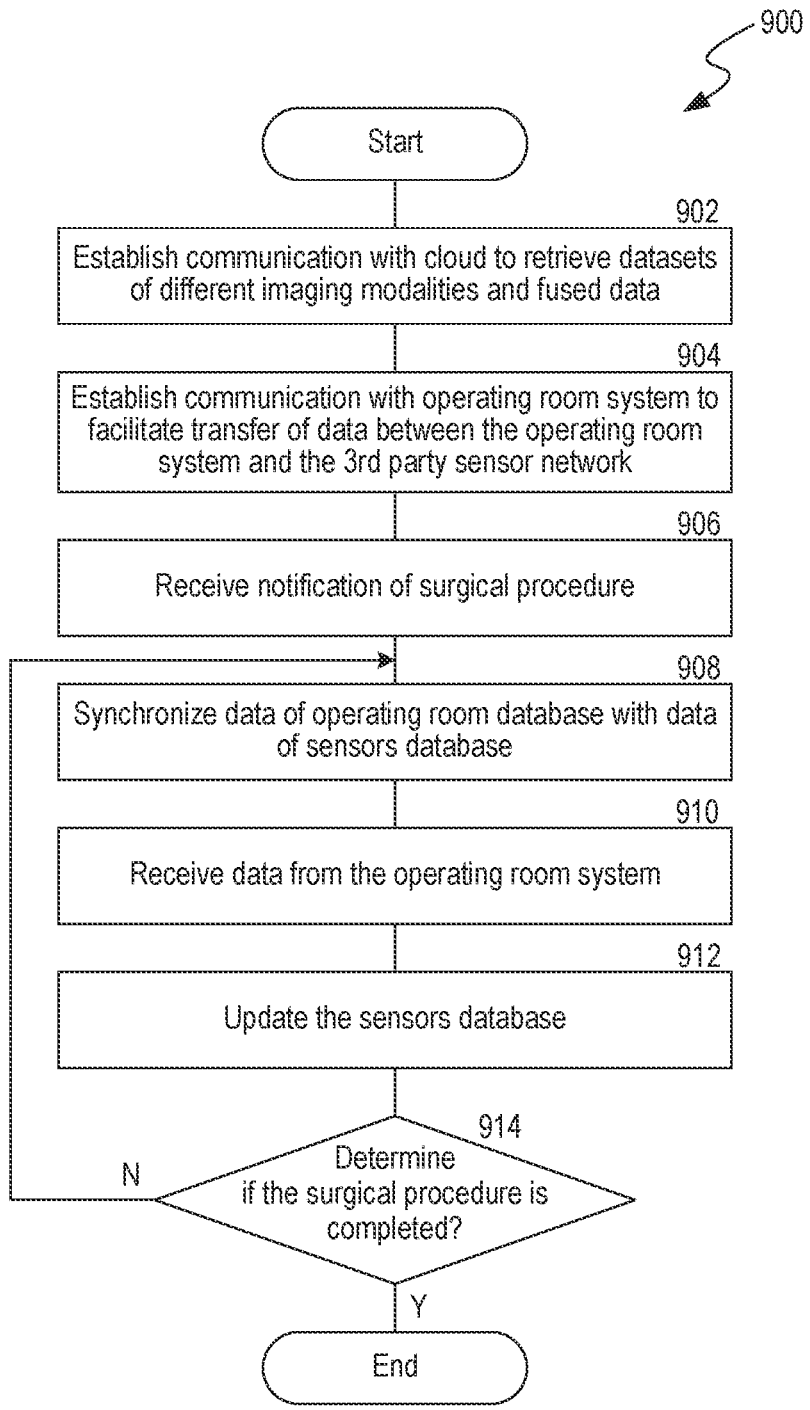
FIG. 9 is a flow diagram illustrating an example process for automated disease detection using multiple-wavelength imaging, in accordance with one or more embodiments.

FIG. 9 is a flow diagram illustrating an example process 900 for automated disease detection using multiple-wavelength imaging, in accordance with one or more embodiments. An example operating room 102 is illustrated and described in more detail with reference to FIG. 1. In some embodiments, the process 900 of FIG. 9 is performed by the third-party sensor network base module 608. The third-party sensor network base module 608 is illustrated and described in more detail with reference to FIG. 6A. In other embodiments, the process 900 of FIG. 9 is performed by a computer system, e.g., the example computer system 300 illustrated and described in more detail with reference to FIG. 3. Particular entities, for example, the console 108 or the robotic surgical system 160 perform some or all of the steps of the process 900 in other embodiments. The console 108 and the robotic surgical system 160 are illustrated and described in more detail with reference to FIG. 1. Likewise, embodiments can include different and/or additional steps, or perform the steps in different orders.

In embodiments, the system 600 determines a first set of (X,Y) data points describing tissue structures of the region of interest using first images (captured using a first imaging modality) and a second set of (X,Y) data points describing the tissue structures using second images (captured using a second imaging modality). For example, in step 902, the third-party sensor network base module 608 establishes communication with the cloud 606 to retrieve datasets of different imaging modalities and fused data. For example, the fused data refers to fused first measurements of physical characteristics of tissue structures and second measurements of the physical characteristics for use by a surgical robot (see FIGS. 4A-4B). The datasets can be used to train a machine learning model on a server, a cloud server, or on a surgical robot (e.g., for edge computing). For example, the third-party sensor network base module 608 retrieves a data set of X-ray images and a data set of ultrasound images, and a fused data set, stored in the cloud 606.

In embodiments, the system 600 establishes communication channels between a first imaging device, a second imaging device, and the machine learning system 200 (see FIG. 2). The machine learning system 200 can be implemented on the third-party sensor network 602, the memory 622, on a cloud server, or on a surgical robot. In embodiments, the machine learning system 200 can be implemented on an imaging device. For example, the third-party sensor network base module 608 establishes communication with the operating room (OR) system 604, over the cloud 606. The communication channels can be implemented using the network adapter 312, network 314, or bus 316 in FIG. 3. For example, in step 904, the third-party sensor network base module 608 establishes communication with the operating room system 604 to facilitate the transfer of data between the operating room system 604 and the third-party sensor network 602. For example, the third-party sensor network base module 608 establishes communication with the operating room system 604, by sending the retrieved data set of the X-ray images and data set of the ultrasound images to the operating room system 604. The stored pictures correspond to the stored data sets of the captured images obtained using the image modalities.

In step 906, the third-party sensor network base module 608 receives notification of the surgical procedure from the operating room system 604. For example, the third-party sensor network base module 608 receives notification from the operating room system 604 that the bone tissue of Alex is to be tested for osteoporosis using a camera. The third-party sensor network base module 608 receives information regarding the X-ray image modality, the ultrasound image modality, and that vital parameters of Alex are a heart rate of 82, SpO2 of 98, and blood pressure of 115/85. Step 908 is described with reference to step 914.

In embodiments, the system 600 locates a particular tissue structure of a region of interest during a surgical procedure by a surgical robot using a fused first set of (X,Y) data points and a second set of (X,Y) data points. For example, the system 600 can use this data to locate tissue structures during a surgical procedure. The data used can be a combination of X-ray and ultrasound measurements used to detect a bone disease. The wavelengths correspond to operating wavelengths of analysis tools or imaging modalities, using electromagnetic or sound waves. In embodiments, the system 600 uses morphological information to perform the location. For example, data from histological images can be used as input to generate clusters using the k-means algorithm. Loose connective tissue, light regions and cell nuclei can be located using the fused first set of (X,Y) data points and second set of (X,Y) data points. For example, tissue features, such as shape and spatial projection are used. In embodiments, the machine learning system 200 (see FIG. 2) is used along with manually annotated images that are used as a ground-truth or for ML training.

In step 910, the third-party sensor network base module 608 receives data related to the multiple components from the operating room system 604. For example, the third-party sensor network base module 608 receives a data set for Picture 2 using the X-ray imaging modality, and for Picture 3 using the ultrasound imaging modality, from the operating room system 604. In embodiments, the third-party sensor network base module 608 generates graphical visualizations of a fused first set of (X,Y) data points and a second set of (X,Y) data points for use by a physician participating in a surgical procedure with the surgical robot. Graphical visualizations are described in more detail with reference to FIG. 1.

In step 912, the third-party sensor network base module 608 updates the sensors database 610. For example, the third-party sensor network base module 608 updates the sensors database 610 with the data set (18, 25) using the X-ray imaging modality and the data set (20, 27) using the ultrasound imaging modality after both these modalities are performed on the bone tissue.

In step 914, the third-party sensor network base module 608 determines whether the surgical procedure is completed according to desired conditions. In one case, the third-party sensor network base module 608 determines that the surgical procedure is not completed based on a status received from the operating room system 604. In this case, the third-party sensor network base module 608 is redirected back to step 908 to synchronize the operating room database 626 with the sensors database 610. The synchronization is related to software and firmware updates to ensure that the operating room system 604 uses the updated software. Further, the synchronization is used to ensure that the date is current so that all time stamps are accurate and historical data is downloaded for reference use in AI/ML applications. In another case, the third-party sensor network base module 608 determines that the surgical procedure is completed based on a status received from the operating room system 604.

FIG. 10 illustrates a structure of an example data chart 1000 for analyzer combinations for automated disease detection using multiple-wavelength imaging, in accordance with one or more embodiments. The system 600 can employ multiple imaging modalities to determine a disease state. In embodiments, the system 600 captures images of a region of interest of a patient's anatomy using a first imaging device and a second imaging device. The first imaging device uses a first imaging modality and the second imaging device uses a second imaging modality. For example, the system 600 uses a combination of the X-ray imaging modality and the ultrasound imaging modality to detect or assess the disease state of the sample. In one example, for detection of osteoporosis, the system uses a camera to capture Picture 1 with the first data set (10, 11) of the bone tissue, and then directs the bone tissue to the X-ray imaging modality to capture Picture 2 with the third data set (11, 13). The system 600 uses the ultrasound imaging modality to capture Picture 3 with the fourth data set (10, 10). The system 600 then evaluates the combined probability from each data set to conclude the diagnosis for osteoporosis. In another example, for detection of a cancerous cell within the bone tissue, a computer tomography (CT) imaging modality and a positron emission tomography (PET) imaging modality are used.

FIG. 11 illustrates a structure of an example data chart 1100 of a variety of disease states detectable by imaging modalities for automated disease detection using multiple-wavelength imaging, in accordance with one or more embodiments. The data chart 1100 can indicate a relationship between the disease state and the plurality of imaging modalities. Further, the data chart 1100 can be used to identify conditions which can be diagnosed, entirely or in part, by using each imaging modality. Further, with each of the imaging modalities for which there is currently no data in the chart, the imaging modalities can identify different diseases like osteoporosis. In one exemplary embodiment, X-rays are used to identify bone degeneration and bone fractures. In another exemplary embodiment, CT imaging is used to identify heart disease and musculoskeletal disorders. In another exemplary embodiment, MRI is used to identify cancerous cells.

FIG. 12 illustrates a structure of an example data chart 1200, in accordance with one or more embodiments. FIG. 12 shows a likelihood of an infection in a localized area when using visible light and infrared imagery for automated disease detection using multiple-wavelength imaging. In embodiments, the system 600 determines a probability that a region of interest is infected using multiple imaging modalities including a first imaging modality and a second imaging modality. The data chart 1200 shows relationships between the wavelengths of light in the visible spectrum and the temperatures taken via infrared imagery to identify the likelihood of an infection in a localized area. In embodiments, the system 600 determines a probability that a region of interest is infected using multiple imaging modalities including a first imaging modality (e.g., visible light) and a second imaging modality (e.g., IR imaging). A likelihood of an infection in the localized area can be identified by comparing data acquired using the multiple imaging modalities. Further, the data from each imaging modality can be fed to an artificial intelligence model or the machine learning (ML) system 200 (see FIG. 2). The AI/ML model can perform edge detection and convolution to analyze the data and compare the data, independently or as an aggregate, to historical data.

In embodiments, independently analyzing data involves creating a probability for an infrared (IR) imaging modality data, and then doing the same for wavelength data, and then averaging or otherwise compiling the data. Alternatively, the data can be compiled before determining a probability or other score representing infection risk. For example, a patient is evaluated for cellulitis. The patient is evaluated using visible light and infrared imaging. In this example, regions with a temperature of 102 degrees Celsius and a wavelength of 100 have a 95.3% likelihood of being infected. An example region includes a transition zone of infected and non-infected tissues and an area of tissue which is clearly not infected.

Figure 13:
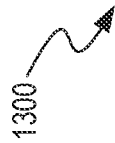
FIG. 13 illustrates a structure of an example data chart showing the likelihood of osteoporosis in a localized area when using X-Ray and ultrasound for automated disease detection using multiple-wavelength imaging, in accordance with one or more embodiments.

FIG. 13 illustrates a structure of an example data chart 1300 showing the likelihood of osteoporosis in a localized area when using x-rays and ultrasounds for automated disease detection using multiple-wavelength imaging, in accordance with one or more embodiments. The data chart 1300 shows relationships between x-ray and ultrasound imaging to identify the likelihood of osteoporosis in a localized area.

In embodiments, the system 600 fuses a first set of (X,Y) data points and a second set of (X,Y) data points to detect a medical condition of the patient. The system 600 updates a surgical robot with the fused first set of (X,Y) data points and the second set of (X,Y) data points for a surgical procedure to be performed on a region of interest by the surgical robot to treat the medical condition. For example, the x-ray imaging modality and the ultrasound imaging modality are employed for the assessment of osteoporosis. In embodiments, x-rays are taken in a first imaging modality and ultrasounds are taken in a second imaging modality. In embodiments, the updating of the surgical robot is performed responsive to a confidence level of the medical condition detection exceeding a threshold. The threshold can be 0.7, 0.8, etc., on a scale of 0 to 1. The threshold can be 90, 99, etc., on a scale of 0-100. For example, when a density of the x-rays taken is 0.5 $g/cm^2$ and an intensity of the ultrasounds taken is 1 arbitrary units (a.u.), the percentage of likelihood of osteoporosis is 98%. An arbitrary unit (or procedure defined unit) refers to a relative unit of measurement to show the ratio of amount of substance, intensity, or other quantities, to a predetermined reference measurement.

In embodiments, the system 600 detects a medical condition of a patient and a confidence level using the machine learning system 200 (see FIG. 2) by correlating a fused first set of (X,Y) data points and second set of (X,Y) data points to stored patient data. A surgical procedure is performed for treating the medical condition. For example, when the density of the x-rays taken is 0.5 g/cm$^2$ and the intensity of the ultrasounds taken is 2 a.u., the percentage of likelihood of osteoporosis is 84.3%. In another example, when the density of the x-rays taken is 0.5 g/cm$^2$ and the intensity of the ultrasounds taken is 3 a.u., then the percentage of likelihood of osteoporosis is 24.1%. Similarly, in another example, when the density of the x-rays taken is 0.5 g/cm$^2$ and the intensity of the ultrasounds taken is 4 a.u., then the percentage of likelihood of osteoporosis is 10.2%. In another example, when the density of the x-rays taken is 0.5 g/cm2 and the intensity of the ultrasounds taken is 5 a.u., then the percentage of likelihood of osteoporosis is 4.3%.

FIG. 14 illustrates a structure of an example data chart 1400 showing the likelihood of cancerous tissue in a localized area when using computer tomography (CT) and positron emission tomography (PET) for automated disease detection using multiple-wavelength imaging, in accordance with one or more embodiments. The data chart 1400 shows relationships between computer tomography (CT) and positron emission tomography (PET) to identify the likelihood of cancerous tissue in a localized area. The CT imaging modality values can be measured in terms of Hounsfield units. The PET imaging modality values can be measured in maximum standardized uptake value (SUVmax).

In embodiments, the system 600 identifies tissue structures using image processing performed on captured images by referencing a fiduciary marker. For example, when the value of the CT imaging modality is measured as −600 units and the SUVmax of the PET imaging modality is 1, then the percentage of likelihood of cancerous tissue is 0.1%. In another example, when the value of the CT imaging modality is measured as −600 units and the SUVmax of the PET imaging modality is 2, then the percentage of likelihood of cancerous tissue is 0.1%, a lesser likelihood. Similarly, in one example, when the value of the CT imaging modality is measured as −600 units and the SUVmax of the PET imaging modality is 3, then the percentage of likelihood of cancerous tissue is 0.1%. Similarly, in another example, when the value of the CT imaging modality is measured as −600 units and the SUVmax of the PET imaging modality is 4, then the percentage of likelihood of cancerous tissue is 0.2%. In another example, when the value of the CT imaging modality is measured as −600 units and the SUVmax of the PET imaging modality is 5, then the percentage of likelihood of cancerous tissue is 0.4%, a medium likelihood. In another example, when the value of the CT imaging modality is measured as −600 units and the SUVmax of the PET imaging modality is 6, then the percentage of likelihood of cancerous tissue is 0.9%, a greater likelihood.

Figure 15:
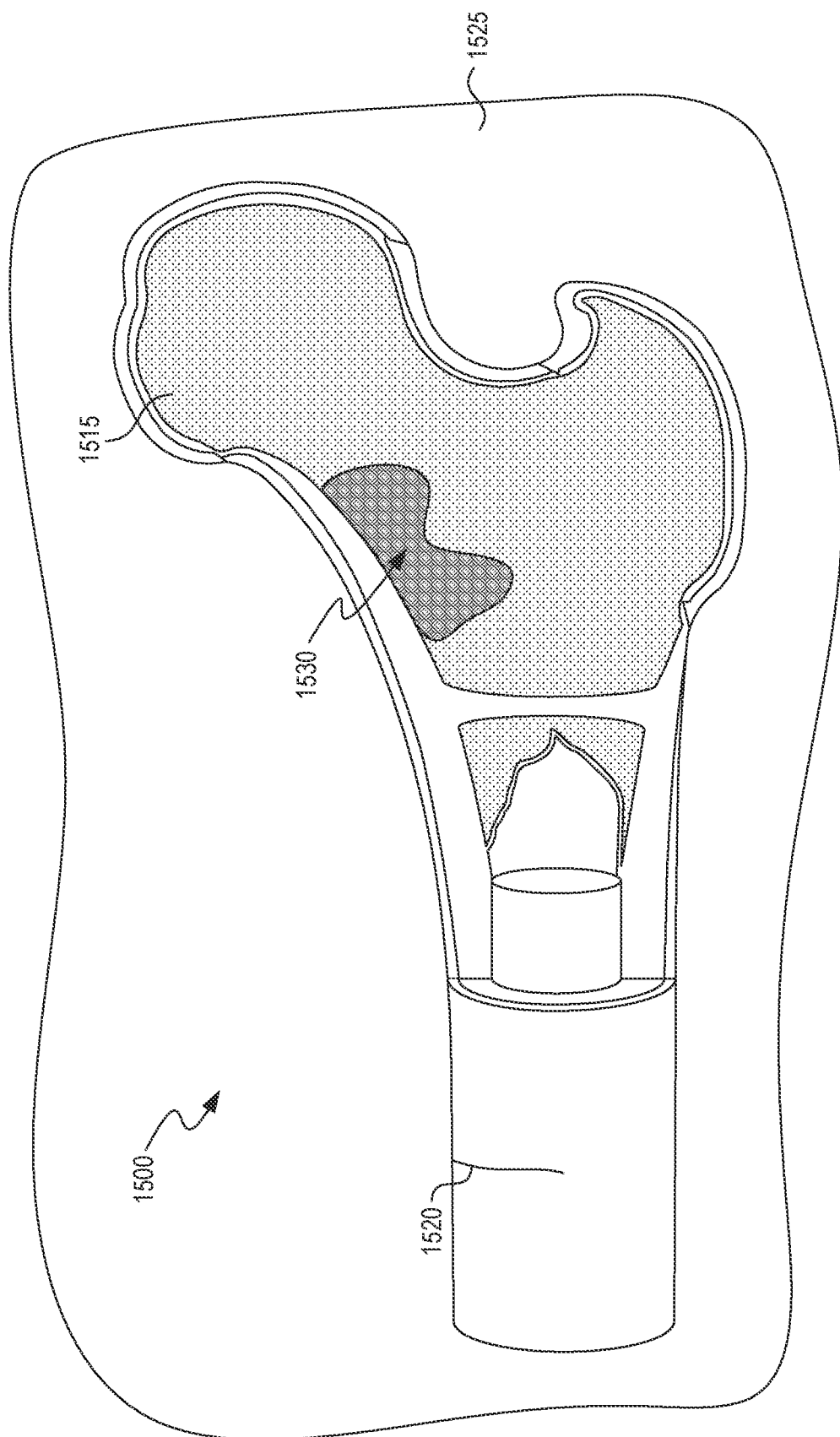
FIG. 15 illustrates an example multi-modality image of a target region, in accordance with one or more embodiments.

FIG. 15 illustrates an example of an image 1500, in accordance with one or more embodiments. The image 1500 can allow a healthcare worker to view a target region 1525 to analyze an automated diagnosis, anatomical features, identify tissue of interest, etc. Systems disclosed herein can analyze a surgical plan to identify potential one or more anatomical features of interest. The system can select imaging modalities based on the potential one or more anatomical features of interest and available imaging modalities. The system can obtain at least one image for each imaging modality and generate a multi-modality image based on each of the obtained images. The system can determine one or more imaging characteristics for each potential anatomical feature of interest and correlate imaging characteristics to identify the available imaging modalities used to select the image modalities. The system can identify anatomical features in the image 1500 (e.g., a pre-operative image, real-time intra-operative image, etc.). The multi-modality image 1500 can be generated based on a surgical plan, physician input, or other input data, and can indicate features (e.g., anatomical elements), margins, tissue type, etc.

To generate the image 1500, systems disclosed herein can receive a tissue density image from an MRI device, a bone fracture image from a CT scanner, a bone degeneration or cancerous tissue image from an ultrasound machine, or images from other imagers disclosed herein. In embodiments, the image 1500 is generated for a surgical plan for treating a damaged bone and can include, for example, tissue density data 1515 (e.g., healthy tissue data from an MRI device), a bone fracture 1520 (e.g., identified using a CT scan), diseased tissue 1530 (e.g., low-density tissue, cancerous tissue, etc., from ultrasound images), or the like. The system can combine the data to generate the image 1500 with features and/or information of interest. In some embodiments, the image 1500 highlights regions 1525 of a tissue sample according to the diagnoses and/or the values from a multi-modality device or multiple imaging devices. For example, the image 1500 can annotate highlight and/or otherwise identify/emphasize features of interest. The emphasis can help direct the doctor's review of the target region 1525 and/or further analysis of the patient. In embodiments, images are generated that include raw data and multi-modality images (e.g., composite images, a multi-layer overlaid image, etc.) to allow a physician to perform an independent diagnosis. In embodiments, the raw data is indicated via differences in shading, color, fill patterns, express indications, display tables, selectable displays, and/or in any other suitable manner.

The multi-modality images can include selectable layers. For example, the multi-modality images can include a first layer created using a first modality, a second layer created using a second modality, and a third layer created using a third modality. A composite layer can include selected data from one or more of the three layers. The number of layers, number of imaging modalities, types of imaging modalities, data sets, fused data sets, and/or image processing (e.g., scaling of images, filtering of images, etc.) can be selected based on target characteristics of the composite layer, surgical plan (e.g., features of interest, anatomical elements, etc.). For example, the image 1500 of FIG. 15 can include selectable layers each with one or more anatomical features identified (e.g., via annotation, false colors, etc.).

The functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any term discussed herein, is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

We claim:

1. A robotic surgical system, comprising:
   a non-transitory computer-readable storage medium storing computer instructions, which when executed by one or more computer processors cause the robotic surgical system to:
   place a fiducial marker in a region of interest of a patient's anatomy;
   capture at least one first image of the region by a first imaging device of medical equipment of the robotic surgical system using a first imaging modality, wherein the fiducial marker is visible in the at least one first image;
   capture at least one second image of the region by a second imaging device of the medical equipment using a second imaging modality different from the first imaging modality, wherein the fiducial marker is visible in the at least one second image;
   identify one or more tissue structures of the region using image processing performed on the at least one first image and the at least one second image by referencing the fiducial marker;
   determine a first set of data points describing the tissue structures using the at least first image and a second set of data points describing the tissue structures using the at least one second image;
   fuse the first set of data points and the second set of data points;
   detect a medical condition of the patient using a machine learning system by:
   determining a first modality value based on the first set of data points of the first imaging modality;
   determining a second modality value based on the second set of data points of the second imaging modality;
   generating an output using a correlation routine based on characterisitics of the first imaging modality and characteristics of the second imaging modality; and
   determining the medical condition using the output from the correlation routine;
   update a surgical robot with the fused first set of data points and second set of data points for a surgical procedure to be performed on the region by the surgical robot for treating the medical condition; and
   generate graphical visualizations of the fused first set of data points and second set of data points for viewing, via a display, by a physician participating in the surgical procedure with the surgical robot.

2. The robotic surgical system of claim 1, wherein the computer instructions cause the robotic surgical system to:
   verify operability of the medical equipment of the robotic surgical system by:
   acquiring one or more test patterns; and
   comparing the one or more test patterns to one or more predetermined values.

3. The robotic surgical system of claim 1, wherein the computer instructions cause the robotic surgical system to:
   determine a probability that the region is infected using a plurality of imaging modalities by identifying a relationship between data acquired using the plurality of imaging modalities.

4. The robotic surgical system of claim 1, wherein the computer instructions cause the robotic surgical system to:
   locate a particular tissue structure in the region during the surgical procedure by a surgical robot based on at least one density value or at least one thickness value of the particular tissue structure in the fused first set of data points and second set of data points.

5. The robotic surgical system of claim 1, wherein the computer instructions cause the robotic surgical system to:
   power on the first imaging device and the second imaging device using a power supply of the robotic surgical system.

6. The robotic surgical system of claim 1, wherein updating the surgical robot is performed responsive to a confidence level of detecting the medical condition exceeding a threshold.

7. The robotic surgical system of claim 1, wherein the computer instructions cause the robotic surgical system to:
   establish communication channels between the first imaging device, the second imaging device, and the machine learning system.

8. A system comprising:
   one or more computer processors; and
   a non-transitory computer-readable storage medium storing computer instructions, which when executed by the one or more computer processors cause the system to:
   place a fiducial marker in a region of interest of a patient's anatomy;
   capture at least one first image of the region by a first imaging device of medical equipment of the system using a first imaging modality, wherein the fiducial marker is visible in the at least one first image;
   capture at least one second image of the region by a second imaging device of the medical equipment using a second imaging modality different from the first imaging modality, wherein the fiducial marker is visible in the at least one second image;
identify one or more tissue structures of the region using image processing performed on the at least one first image and the at least one second image by referencing the fiducial marker;
determine a first set of data points describing the tissue structures using the at least first image and a second set of data points describing the tissue structures using the at least one second image;
fuse the first set of data points and the second set of data points;
detect a medical condition of the patient using a machine learning system by:
determining a first modality value based on the first set of data points of the first imaging modality;
determining a second modality value based on the second set of data points of the second imaging modality;
generating an output using a correlation routine based on characteristics of the first imaging modality and characterisitics of the second imaging modality; and
determining the medical condition using the output from the correlation routine;
update a surgical robot with the fused first set of data points and second set of data points for a surgical procedure to be performed on the region by the surgical robot for treating the medical condition; and
generate graphical visualizations of the fused first set of data points and second set of data points for viewing, via a display, by a physician participating in the surgical procedure with the surgical robot.

9. The system of claim 8, wherein the computer instructions cause the system to:
verify operability of the medical equipment of the robotic surgical system by:
acquiring one or more test patterns; and
comparing the one or more test patterns to one or more predetermined values.

10. The system of claim 8, wherein the computer instructions cause the system to:
determine a probability that the region is infected using a plurality of imaging modalities by identifying a relationship between data acquired using the plurality of imaging modalities.

11. The system of claim 8, wherein the computer instructions cause the system to:
locate a particular tissue structure in the region during the surgical procedure by a surgical robot based on at least one density value or at least one thickness value of the particular tissue structure in the fused first set of data points and second set of data points.

12. The system of claim 8, wherein the computer instructions cause the system to:
power on the first imaging device and the second imaging device using a power supply of the robotic surgical system.

13. The system of claim 8, wherein updating the surgical robot is performed responsive to a confidence level of detecting the medical condition exceeding a threshold.

14. A method for operating a robotic surgical system, comprising:
placing a fiducial marker in a region of interest of a patient's anatomy;
capturing at least one first image of the region by a first imaging device of medical equipment of the robotic surgical system using a first imaging modality, wherein the fiducial marker is visible in the at least one first image;
capturing at least one second image of the region by a second imaging device of the medical equipment using a second imaging modality different from the first imaging modality, wherein the fiducial marker is visible in the at least one second image;
identifying one or more tissue structures of the region using image processing performed on the at least one first image and the at least one second image by referencing the fiducial marker;
determining a first set of data points describing the tissue structures using the at least first image and a second set of data points describing the tissue structures using the at least one second image;
fusing the first set of data points and the second set of data points;
detecting a medical condition of the patient using a machine learning system by:
determining a first modality value based on the first set of data points of the first imaging modality;
determining a second modality value based on the second set of data points of the second imaging modality;
generating an output using a correlation routine based on characteristics of the first imaging modality and characteristics of the second imaging modality; and
determining the medical condition using the output from the correlation routine;
updating a surgical robot with the fused first set of data points and second set of data points for a surgical procedure to be performed on the region by the surgical robot for treating the medical condition; and
generating graphical visualizations of the fused first set of data points and second set of data points for viewing, via a display, by a physician participating in the surgical procedure with the surgical robot.

15. The method of claim 14, comprising:
verifying operability of the medical equipment of the robotic surgical system by:
acquiring one or more test patterns; and
comparing the one or more test patterns to one or more predetermined values.

16. The method of claim 14, comprising:
determining a probability that the region is infected using a plurality of imaging modalities by identifying a relationship between data acquired using the plurality of imaging modalities.

17. The method of claim 14, comprising:
locating a particular tissue structure in the region during the surgical procedure by a surgical robot based on at least one density value or at least one thickness value of the particular tissue structure in the fused first set of data points and second set of data points.

18. The method of claim 14, comprising:
powering on the first imaging device and the second imaging device using a power supply of the robotic surgical system.

19. The method of claim 14, wherein updating the surgical robot is performed responsive to a confidence level of detecting the medical condition exceeding a threshold, wherein the correlation routine includes a Pearson correlation, a Kendall rank correlation, a Spearman correlation or a Point-Biserial correlation.

20. The method of claim 14, comprising:

establishing communication channels between the first imaging device, the second imaging device, and the machine learning system.

\* \* \* \* \*